United States Patent
Baranski et al.

(10) Patent No.: US 10,398,200 B2
(45) Date of Patent: Sep. 3, 2019

(54) DYNAMIC FIT ADJUSTMENT FOR WEARABLE ELECTRONIC DEVICES

(71) Applicant: Apple Inc., Cupertino, CA (US)

(72) Inventors: Andrzej T. Baranski, Santa Clara, CA (US); Serhan O. Isikman, Sunnyvale, CA (US); Tyler S. Bushnell, Mountain View, CA (US); Steven J. Martisauskas, Menlo Park, CA (US); David I. Nazzaro, Groveland, MA (US)

(73) Assignee: APPLE INC., Cupertino, CA (US)

( * ) Notice: Subject to any disclaimer, the term of this patent is extended or adjusted under 35 U.S.C. 154(b) by 0 days.

(21) Appl. No.: 16/197,100

(22) Filed: Nov. 20, 2018

(65) Prior Publication Data

US 2019/0082800 A1 Mar. 21, 2019

Related U.S. Application Data

(63) Continuation of application No. 15/728,349, filed on Oct. 9, 2017, now Pat. No. 10,149,521, which is a continuation of application No. 14/691,217, filed on Apr. 20, 2015, now Pat. No. 9,781,984.

(60) Provisional application No. 62/129,950, filed on Mar. 8, 2015.

(51) Int. Cl.
| *A44C 5/00* | (2006.01) |
| *A44C 5/20* | (2006.01) |
| *A45F 5/00* | (2006.01) |
| *A61B 5/00* | (2006.01) |
| *A44C 5/08* | (2006.01) |

(52) U.S. Cl.
CPC .......... *A44C 5/2071* (2013.01); *A44C 5/0069* (2013.01); *A44C 5/20* (2013.01); *A44C 5/0053* (2013.01); *A44C 5/08* (2013.01); *A45F 2005/008* (2013.01); *A61B 5/681* (2013.01)

(58) Field of Classification Search
CPC ................. A61B 17/1325; A61B 5/681; A45F 2005/008; Y10T 24/4782; A43C 11/165; A63B 2220/836; A44C 5/0053
USPC .................... 224/221, 176; 24/68 J, 265 WS
See application file for complete search history.

(56) References Cited

U.S. PATENT DOCUMENTS

| 1,313,644 A | 8/1919 | Simon |
| 1,692,079 A | 11/1928 | D'Alo |
| 1,817,475 A | 8/1931 | Becker |
| 3,890,801 A | 6/1975 | Newman |
| 4,941,236 A | 7/1990 | Sherman et al. |

(Continued)

FOREIGN PATENT DOCUMENTS

| CN | 2862782 Y | 1/2007 |
| CN | 201683167 U | 12/2010 |

(Continued)

*Primary Examiner* — Justin M Larson
(74) *Attorney, Agent, or Firm* — Morgan, Lewis & Bockius LLP

(57) ABSTRACT

Systems and methods for dynamically adjusting the fit of a wearable electronic device are disclosed. In many embodiments, a tensioner associated with a wearable electronic device can control one or more actuators that are mechanically coupled to either the housing or to a band attached to the wearable electronic device. In one example, in response to a signal to increase the tightness of the band, the tensioner can cause the actuator(s) to increase the tension within the band.

19 Claims, 26 Drawing Sheets

(56) References Cited

U.S. PATENT DOCUMENTS

| | | |
|---|---|---|
| 5,485,848 A | 1/1996 | Jackson |
| 5,509,423 A | 4/1996 | Bryars |
| 6,151,968 A | 11/2000 | Chou |
| 6,251,080 B1 | 6/2001 | Henkin |
| 6,301,754 B1 | 10/2001 | Grunberger et al. |
| 6,461,125 B1 | 10/2002 | Terasawa |
| 6,648,502 B2 | 11/2003 | Oomori |
| 6,799,887 B1 | 10/2004 | Kinney |
| 7,562,640 B2 | 7/2009 | Lalor |
| 7,618,384 B2 | 11/2009 | Nardi |
| 7,690,220 B2 | 4/2010 | Okamura |
| 7,752,774 B2 | 7/2010 | Ussher |
| 8,147,417 B2 | 4/2012 | Gavriely |
| 8,370,998 B2 | 2/2013 | Han |
| 8,522,456 B2 | 9/2013 | Beers |
| 8,769,844 B2 | 7/2014 | Beers et al. |
| 9,044,372 B2 | 6/2015 | Wild |
| 9,129,503 B2 | 9/2015 | Borlenghi |
| 9,144,168 B2 | 9/2015 | Sedillo |
| 9,144,273 B2 | 9/2015 | Wu |
| 9,204,690 B1 | 12/2015 | Alt |
| 9,307,804 B2 | 4/2016 | Beers |
| 9,365,387 B2 | 6/2016 | Beers |
| 9,471,102 B2 | 10/2016 | Townsend |
| 9,770,624 B2 | 9/2017 | Bender |
| 9,781,984 B2 | 10/2017 | Baranski |
| 10,082,872 B2 * | 9/2018 | Cruz-Hernandez ..... G06F 1/163 |
| 10,143,271 B2 * | 12/2018 | Zhang ..................... A44C 5/04 |
| 2004/0025984 A1 | 2/2004 | Holemans |
| 2007/0125816 A1 | 6/2007 | Myers |
| 2008/0060224 A1 | 3/2008 | Whittlesey |
| 2008/0086911 A1 | 4/2008 | Labbe |
| 2012/0102691 A1 | 5/2012 | Han |
| 2014/0070042 A1 | 3/2014 | Beers |
| 2014/0094728 A1 | 4/2014 | Soderberg |
| 2015/0065891 A1 | 3/2015 | Wiesel |
| 2015/0135410 A1 | 5/2015 | Wu |
| 2016/0255944 A1 | 9/2016 | Baranski |
| 2016/0272458 A1 | 9/2016 | Beers |
| 2016/0324470 A1 | 11/2016 | Townsend |
| 2016/0345653 A1 | 12/2016 | Beers |
| 2016/0345661 A1 | 12/2016 | Beers |
| 2017/0035355 A1 | 2/2017 | Chen |
| 2017/0086743 A1 | 3/2017 | Bushnell |

FOREIGN PATENT DOCUMENTS

| | | |
|---|---|---|
| CN | 201846934 U | 6/2011 |
| CN | 201869909 U | 6/2011 |
| CN | 102488365 A | 6/2012 |
| JP | S 59-186504 | 10/1984 |
| JP | 2010-207411 | 9/2010 |
| KR | 20080000609 | 1/2008 |

* cited by examiner

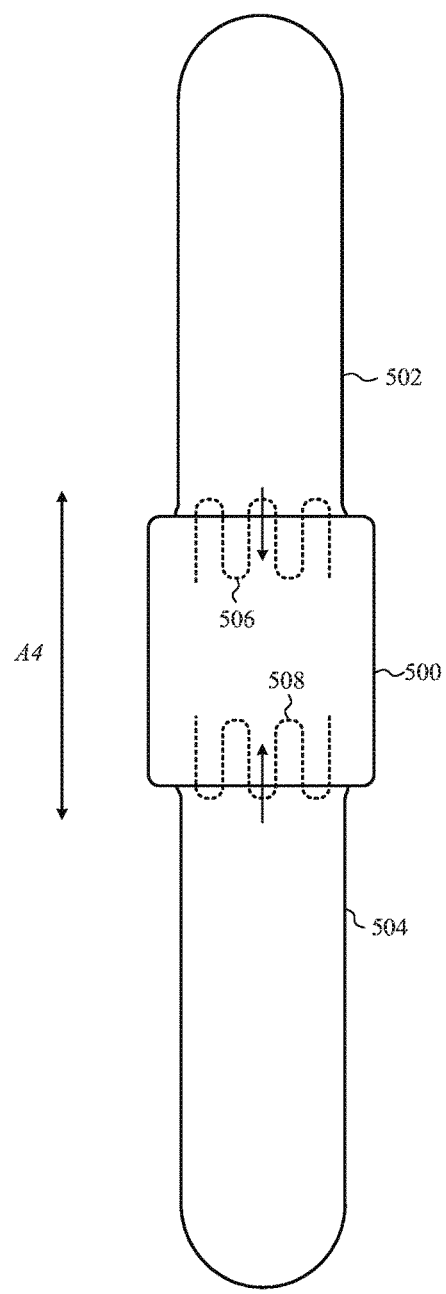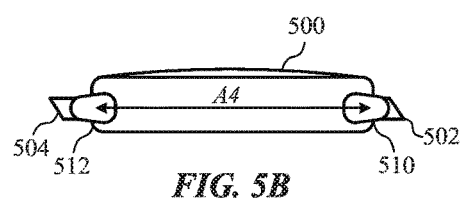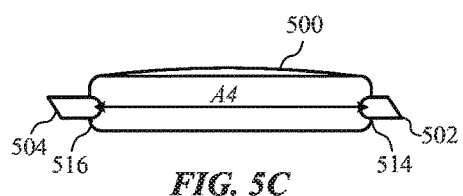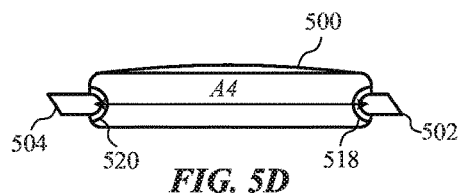

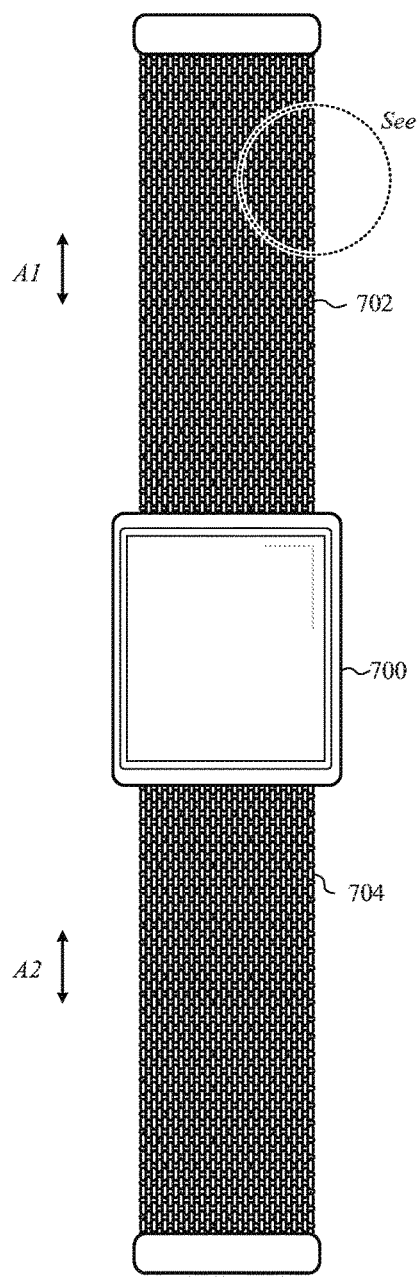
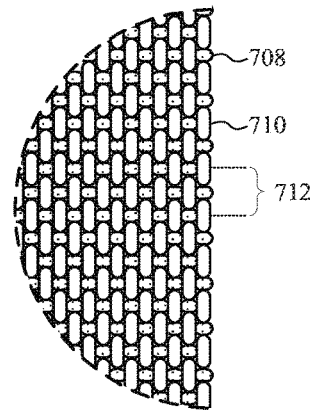
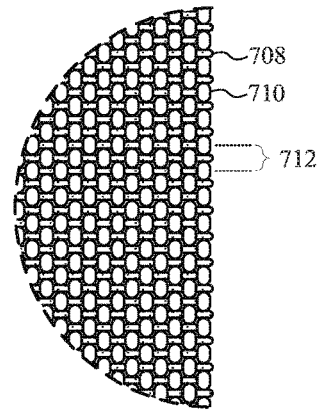
*FIG. 7A*
*FIG. 7B*
*FIG. 7C*

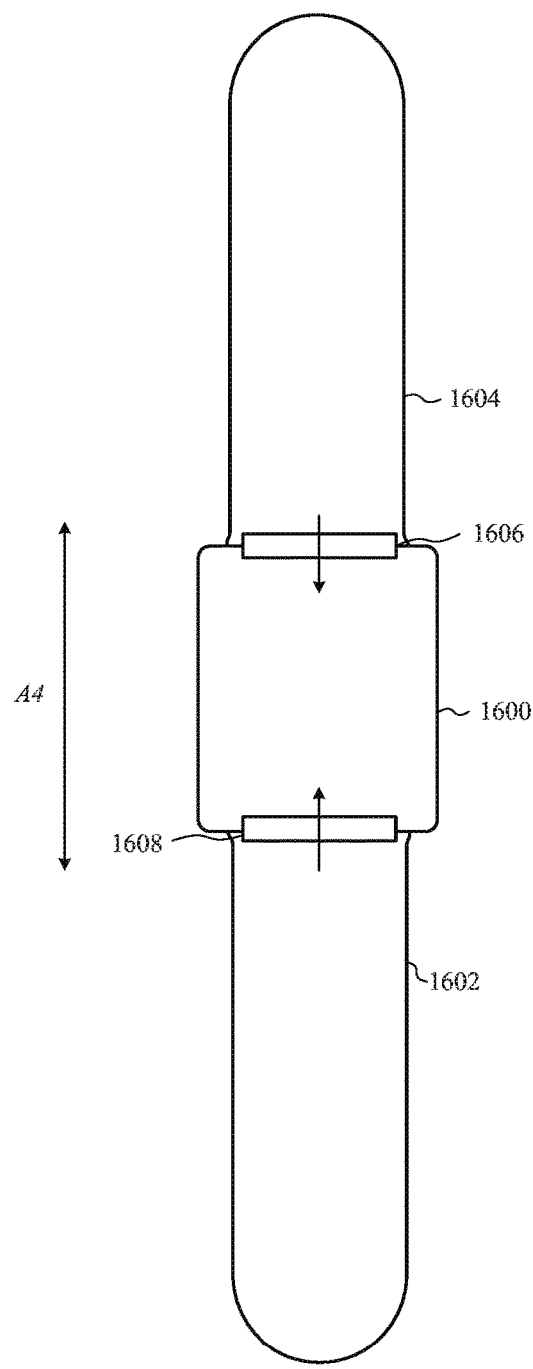 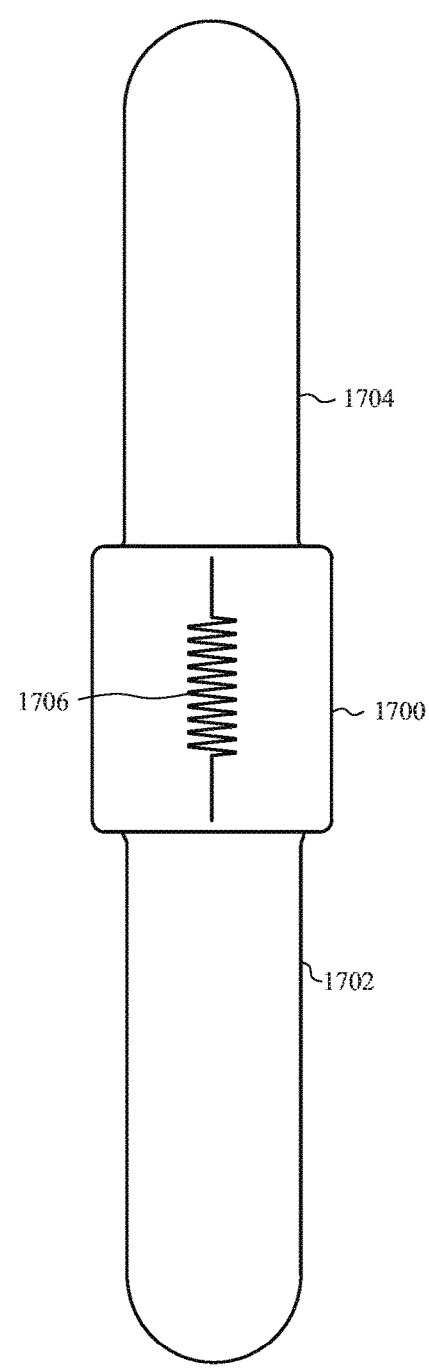
*FIG. 16*  *FIG. 17*

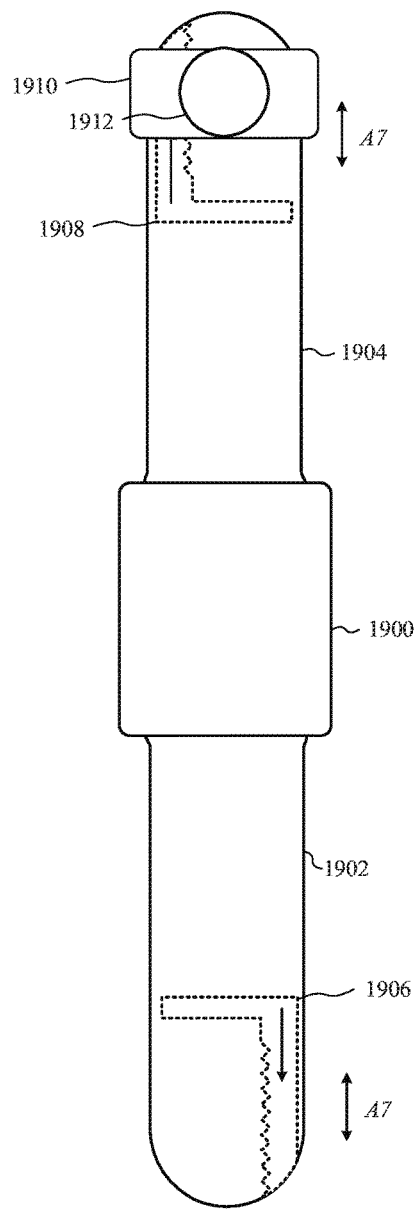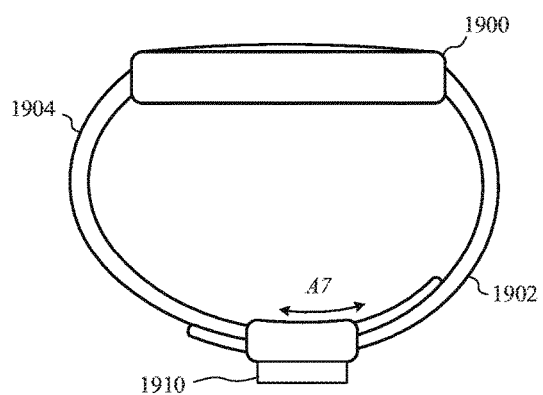
*FIG. 19A*
*FIG. 19B*

DYNAMIC FIT ADJUSTMENT FOR WEARABLE ELECTRONIC DEVICES

CROSS-REFERENCE TO RELATED APPLICATIONS

This application is a continuation of Ser. No. 15/728,349, filed Oct. 9, 2017, which is a continuation of U.S. patent application Ser. No. 14/691,217, filed Apr. 20, 2015, now issued as U.S. Pat. No. 9,781,984, which claims the benefit of U.S. Provisional Patent Application No. 62/129,950, filed Mar. 8, 2015 and titled "Dynamic Adjustment for Wearable Electronic Devices," the disclosures of which are hereby incorporated herein by reference in their entirety.

TECHNICAL FIELD

Embodiments described herein relate to systems and methods for affixing an electronic device to an object and, more particularly, to systems and methods for dynamic adjustment of the fit of wearable electronic devices.

BACKGROUND

Some electronic devices may be removably attached to a user. For example, a wristwatch or fitness/health tracking device can be attached to a user's wrist by joining free ends of a watch band together.

In many cases, watch bands may have limited fit adjustment increments available. For example, some bands have an incrementally user-adjustable size (e.g., a buckling clasp, pin and eyelet, etc.) whereas other bands have a substantially fixed size, adjustable only with specialized tools and/or expertise (e.g., folding clasp, deployment clasp, snap-fit clasp, etc.). Still other bands may be elasticated expansion-type bands that stretch to fit around a user's wrist.

In many cases, conventional watch bands may catch, pinch, or pull a user's hair or skin during use if the band is overly tight. In other cases, watch bands may slide along a user's wrist, turn about a user's wrist, or may be otherwise uncomfortable or bothersome to a user if the band is overly loose. These problems can be exacerbated during periods of heightened activity, such as while running or playing sports. Furthermore, adjusting the size or fit of conventional watch bands often requires multiple steps, specialized tools, and/or technical expertise. In other cases, sizing options available to a user may be insufficient to obtain a proper fit. In still further examples, the fit may be different and/or may be perceived to be different given certain environmental (e.g. temperature, humidity) or biological conditions (e.g., sweat, inflammation). As a result, users of conventional wristwatches and/or fitness/health tracking devices may select a tolerable (although not optimally comfortable) fit, reserving tight bands for fitness/health tracking devices and loose bands for conventional wristwatches.

However, some wearable electronic devices (such as smart watches) may be multi-purpose devices, providing in one example both fitness/health tracking and timekeeping functionality. Accordingly, a user may prefer the fit of a smart watch to vary with use. For example, a user may prefer a looser fit in a timekeeping mode and a tighter fit in a fitness/health tracking mode.

Accordingly, there may be a present need for systems and methods for dynamic adjustment of the fit of wearable electronic devices.

SUMMARY

Embodiments described herein may relate to, include, or take the form of a method of adjusting the fit of a wearable electronic device secured by a band to a user, the method including at least the operations of receiving a signal with an instruction to adjust the fit of the band, selecting an operational mode (e.g., tightening mode, loosening mode, flexibility mode, rigid mode, etc.) of a tensioner coupled to electronic device, and actuating the tensioner based on the instruction.

Further embodiments described herein may relate to, include, or take the form of a method of soliciting attention of a user by adjusting the fit of a wearable electronic device secured to the user by a band, the method including at least the operations of receiving an instruction to solicit attention of the user, and in response, actuating a tensioner coupled to the wearable electronic device to cause an increase in the tightness of the band.

Other embodiments described herein may relate to, include, or take the form of a method of restraining a wearable electronic device secured by a strap to a user engaged in physical activity, the method including at least the operations of receiving an indication that the user may be engaged in physical activity, and in response, actuating a tensioner coupled to the wearable electronic device to increase the tightness of the strap.

BRIEF DESCRIPTION OF THE DRAWINGS

Reference will now be made to representative embodiments illustrated in the accompanying figures. It should be understood that the following descriptions are not intended to limit the disclosure to one preferred embodiment. To the contrary, each is intended to cover alternatives, modifications, and equivalents as may be included within the spirit and scope of the described embodiments as defined by the appended claims.

FIG. 5A depicts a top plan view of an example wearable electronic device with a two-piece band system configured to retract into the body of the wearable electronic device in response to an electrical signal from a tensioner.

FIG. 5B depicts a side plan view of the example wearable electronic device of FIG. 5A showing a lug-based band attachment system.

FIG. 5C depicts another side plan view of the example wearable electronic device of FIG. 5A showing a channel-based attachment system.

FIG. 5D depicts another side plan view of the example wearable electronic device of FIG. 5A showing a permanent attachment system.

FIG. 7A depicts a top plan view of an example wearable electronic device with a woven band system configured to contract along its length and/or width in response to an electrical signal from a tensioner.

FIG. 7B depicts a detail view of the example wearable electronic device of FIG. 7A.

FIG. 7C depicts a detail view of the example wearable electronic device of FIG. 7A, showing the woven band system in a contracted configuration.

FIG. 16 depicts a top plan view of an example wearable electronic device with another two-piece band system configured to retract toward the body of the wearable electronic device in response to an electrical signal from a tensioner.

FIG. 17 depicts a top plan view of an example wearable electronic device with another two-piece band system configured to retract into the body of the wearable electronic device in response to an electrical signal from a tensioner.

FIG. 19A depicts a top plan view of an example wearable electronic device with another two-piece band system configured to contract along its length in response to an electrical signal from a tensioner or in response to a user input.

FIG. 19B depicts a side plan view of the example wearable electronic device of FIG. 19A in a closed configuration.

The use of the same or similar reference numerals in different drawings can indicate similar, related, or identical items.

DETAILED DESCRIPTION

Figure 1A:
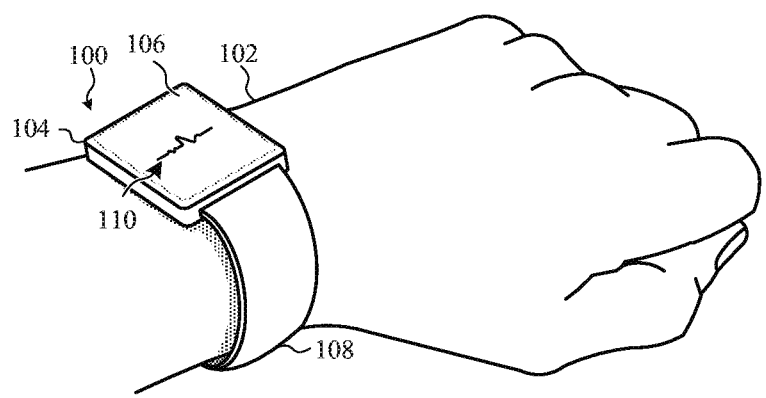
FIG. 1A depicts a perspective view of an example wearable electronic device loosely attached by a band to a user.

Embodiments described herein relate to systems and methods for dynamic adjustment of the fit of wearable electronic devices. It should be appreciated that the various embodiments described herein, as well as functionality, operation, components, and capabilities thereof may be combined with other elements, embodiments, structures and the like, and so any physical, functional, or operational discussion of any element or feature is not intended to be limited solely to a particular embodiment to the exclusion of others.

As noted above, many portable electronic devices may be removably attached to a user. In some examples, a heart rate sensor may be attached to a user's chest by a strap. In another example, a portable audio player may be secured to a user's arm by inserting the player into an armband case. In another example, a wearable electronic device such as a smart watch or a fitness device can be attached to a user's wrist by joining free ends of a conventional watch band together. In other examples, a clasp or an elasticated band may be used to secure the wearable electronic device.

Although many embodiments are described herein with reference to wrist bands for attaching a wrist-worn electronic device to a user, one may appreciate that other form factors may be favored in other embodiments. In other words, the methods, systems, and techniques described herein with illustrative reference to wrist-worn devices may be equally applied to non-wrist worn devices. For example, in other embodiments, devices may be configured to attach to other limbs or body portions (e.g., necklaces, arm bands, waistbands, ear hooks, finger rings, anklets, toe rings, chest wraps, head bands, etc.). Furthermore, other embodiments described herein may be applied to dynamically adjust the fit of an electronic device to a non-user object such as a charging stand or station. In other embodiments, an electronic device can be fit to another biological subject such as an animal (e.g., pet collar).

As noted above, many conventional watch bands may be uncomfortable, painful, or bothersome if improperly fit to a user. For example, a user's skin and/or hair may be pinched or pulled if a conventional watch band is improperly fit. In another example, a user may be irritated by a watch that slides up and down a user's wrist and/or rotates about the user's wrist during use.

In other cases, the fit of a conventional watch band may be different and/or may be perceived to be different given different situations. For example, in humid conditions, the fit of a band may be perceived to be tighter. In another example, a user who is sweating may perceive the fit of a band to be looser. In many cases, these problems can be exacerbated during periods of heightened activity, such as while running or playing sports.

Despite the prevalence of issues associated with improperly fit bands, adjusting the size or fit of conventional watch bands often requires multiple steps, specialized tools, and/or technical expertise. For example, a metal link band may require specialized tools to remove one or more links of the band to resize the band. In other cases, a leather band with a deployment clasp may need to be physically cut to size in order to resize the band.

In other cases, watch bands may have limited fit adjustment increments available. For example, a conventional watch band may space sizing eyelets approximately 8 mm apart. In some cases, a user may prefer a fit corresponding to a location between two eyelets. In some examples, especially for users having relatively small wrists, an error of ±4 mm (e.g., example of error halfway between "too tight" and "too loose") can correspond to an error upwards of ±5% of the circumference of that user's wrist, which, for many users, may be intolerable.

As a result, users of conventional wristwatches and/or fitness/health tracking devices may select a tolerable (although not optimally comfortable) fit, reserving tighter bands for fitness/health tracking devices and looser bands for conventional wristwatches.

However, as noted above, some wearable electronic devices, such as smart watches, may be multi-purpose devices. For example, many smart watches provide both fitness/health tracking and timekeeping functionality. Thus, many users may wear a smart watch exclusively, instead of periodically switching between wearing a traditional wristwatch and a separate fitness/health tracking device. In these examples, a user may prefer the fit of a smart watch to vary with use. For example, a user may prefer a looser fit in a timekeeping mode and a tighter fit in a fitness/health tracking mode.

As may be appreciated, the inconvenience associated with repeated resizing and reattachment of a conventional watchband may contribute to diminishing use of a wearable electronic device, which may, in turn, precipitate a customer retention problem for the manufacturer thereof. In other examples, such as for wearable electronic devices configured to collect health-related information (e.g., pulse rate, blood oxygen saturation, blood pressure, insulin levels, etc.) or to provide health-related notifications (e.g., prescription timing reminders, medical alerts, medical identification numbers, etc.), discontinued use of the wearable electronic device may lead to more serious consequences such as health problems, medical emergencies, and/or incomplete or inconsistent medial data collection.

Accordingly, many embodiments described herein relate to systems and methods for dynamic adjustment of the fit of the wearable electronic devices.

For example, certain embodiments described herein take the form of methods for adjusting the fit of a wearable electronic device secured by a band to a user, the method including the operations of receiving a signal with an instruction to adjust the fit of the band, selecting an operational mode (e.g., tightening mode, loosening mode, flexibility mode, rigid mode, etc.) of a tensioner coupled to electronic device, and actuating the tensioner based on the instruction.

In some embodiments, the signal received in the course of operating methods described herein may be generated within the wearable electronic device itself. For example, a wearable electronic device such as a smart watch may periodically adjust its own fit. In other examples, the wearable electronic device can generate the signal in response to input from a user. For example, a user can provide input to a touch screen of the wearable electronic device to indicate to the wearable electronic device the user's desire for the fit of the device to change, either with increased tightness or decreased tightness.

In another example, the signal received may be generated by a secondary electronic device in communication with the wearable electronic device. For example, in some embodiments, a personal cellular phone in communication with a wearable electronic device can provide a signal to the wearable electronic device to adjust the fit thereof. In still further embodiments, the signal received may be generated by a network device such as a server. In these examples, the server in communication with the wearable electronic device can provide a signal to the wearable electronic device to adjust the fit thereof.

In many cases, the instruction associated with the signal received in the course of operating methods described herein may include one or more values that correspond to a mode with which the fit of the wearable electronic device should be changed. For example, in some embodiments, the instruction can include a value or pointer (e.g., selection bit, function name, etc.) that indicates the tightness of the fit of the wearable electronic device should increase, corresponding to a tightening mode. In another example, the instruction can include a value or pointer that indicates the tightness of the fit of the wearable electronic device should decrease, corresponding to a loosening.

In further examples, the instruction can also include a value or pointer corresponding to an amount or magnitude of change, either relative or absolute. For example, an instruction as described above can include a value or pointer indicating that the fit should be changed by 5%. In another example, an instruction as described above can include a value or pointer indicating that the fit should be changed by shortening a band by 1 mm. In another example, an instruction as described above can include a value or pointer indicating that the fit should be changed by extending a portion of the housing of the wearable electronic device by 3 mm. In another example, an instruction as described above can include a value or pointer indicating that the fit should be change by applying a force of 0.1 Newtons to the band. In other embodiments, other values and/or pointers may be used.

In further examples, the instruction can include a value or pointer corresponding to a threshold of change. For example, an instruction as described above can include a value or pointer indicating that the fit should be changed by extending a portion of the housing of the wearable electronic device until the portion comes into contact with the user's skin and applies pressure of 1,000 N/m$^2$ (e.g., 0.15 psi). In other embodiments, other threshold values and/or pointers may be used.

In many cases, and as described above, the instruction may be subdivided into multiple parts (or subcomponents) including, in some examples, a mode, a magnitude, and/or a threshold. In this manner, a variety of functions can be performed. For example, a band can tighten or loosen without a target (e.g., "become generally tighter" or "become generally looser"), can tighten or loosen by an increment (e.g., "become X tighter" or "become X looser"), can tighten or loosen until a threshold is reached (e.g., "become tighter until" or "become looser until"), apply a specific value of greater or less tightness (e.g., "apply tightness X"), apply a tightness or looseness as a function of time (e.g., "become tighter for 1 second, then loosen").

As noted above, a tensioner can be coupled to the wearable electronic device. In many cases, a tensioner can be an analog, digital, or integrated circuit configured to apply an electrical signal to cause tension (either directly or indirectly) to be applied to, or relieved form, the band. In other cases, a tensioner can be a physical apparatus such as a motor, electromagnetic coil, or solenoid that can be actuated to cause tension (either directly or indirectly) to be applied to, or relieved form, the band. Accordingly, the term "tensioner" and related phrases and terminology is used herein to generally refer to a circuit, apparatus, controller, or program code executed by a processor, that is configured to cause, either directly or indirectly, tension in a band or strap coupled to an electronic device housing to increase or decrease.

In some examples, a tensioner associated with and/or coupled to the wearable electronic device can also be coupled to a portion of the band that is configured to compress in response to an electrical signal. For example, a shape memory wire such as Nitinol can be formed in a longitudinal serpentine pattern within one or more portions of a band. The tensioner can increase a current (or voltage) applied to the Nitinol in response to an instruction to increase the tightness of the band or can decrease a current (or voltage) applied to the Nitinol in response to an instruction to decrease the tightness of the band. In response to the increase or decrease in the length of the longitudinal and serpentine Nitinol, the band can experience an increase or decrease in length which, in turn, can cause an increase or decrease the tightness of the fit of the band.

In other examples, Nitinol can be formed in a serpentine pattern through the thickness or width of one or more portions of a band. In these embodiments, the tensioner can increase a current (or voltage) applied to the Nitinol in response to an instruction to decrease the tightness of the band and, correspondingly, can decease a current (or voltage) applied to the Nitinol in response to an instruction to increase the tightness of the band. In response to the increase or decrease in the width and/or thickness of the band, the band can experience a respective decrease or increase in length which, in turn, decreases or increases the tightness of the fit of the band.

In some examples, one or more portions of a band can include a bladder in communication with a pump or actuator disposed within the housing of the wearable electronic device. The tensioner may be configured to control the pressure applied by the pump to a fluid in communication with the bladder. In some cases the fluid can be a gas or a liquid. For example, in some embodiments, air can be used as the fluid in communication with the bladder. In other cases, a liquid with a low viscosity such as oil or water can be used as the fluid in communication with the bladder. In these embodiments, the tensioner can increase the pressure applied by the pump to the fluid in response to an instruction to increase the tightness of the band or can decrease the pressure applied by the pump in response to an instruction to decrease the tightness of the band. In response to the increase or decrease in pressure, the bladder can experience an increase or decrease in volume, which, in turn, increases or decreases the tightness of the band.

In another embodiment, the tensioner can be connected to a coupling that joins the band at one or more points to the housing of the wearable electronic device. In some examples, the coupling can be a lug that extends from the housing of the wearable electronic device. In such an embodiment, the tensioner can withdraw the coupling into the housing of the wearable electronic device in response to an instruction to increase the tightness of the band or can extend the coupling from the housing of the wearable electronic device in response to an instruction to decrease the tightness of the band.

In another embodiment, the tensioner can be connected to an extendable portion of the housing of the wearable electronic device oriented to extend toward (or retract from) the user's skin. For example, in certain embodiments the extendable portion can extend toward a user's wrist or, in other examples, the extendable portion can retract from the user's wrist. In such an embodiment, the tensioner can extend the extendable portion in response to an instruction to increase the tightness of the band or can withdraw the extendable portion into the housing of the wearable electronic device in response to an instruction to decrease the tightness of the band.

In other embodiments, the tensioner may be coupled to, or configured to control the operation of, one or more mechanisms, components, or apparatuses capable to reduce or increase one or more dimensions of the band. For example, in some cases, the tensioner can be coupled to an apparatus capable to increase or decrease the length of the band. In another example, the tensioner can be coupled to an apparatus capable to increase or decrease the thickness of the band. In other examples, the tensioner can be coupled to an apparatus capable to increase or decrease the width of the band. In still further examples, the tensioner can be coupled to an apparatus capable to increase or decrease the rigidity of the band.

In other embodiments, the tensioner may be coupled to, or configured to control the operation of, one or more mechanisms, components, or apparatuses capable to reduce or increase one or more dimensions of the housing of the wearable electronic device. For example, as noted above, in some cases the tensioner can be coupled to an extendable portion that can extend toward or retract from a user's skin. In other examples, the tensioner can be coupled to a portion of the wearable electronic device housing that is configured to couple to the band itself. For example, as noted above, the tensioner of some embodiments can be coupled to an apparatus capable to withdraw into the housing of the wearable electronic device and also configured to extend from the housing of the wearable electronic device. In still further embodiments, alternative tensioner, band, and/or housing configurations, topologies, and interactions are contemplated.

For example, some embodiments may include a configuration in which the instruction received in the course of operating methods described herein may be based on a user input to the wearable electronic device. For example, a user may provide input to the wearable electronic device via one or more input mechanisms such as a touch screen to indicate the user's preference for the fit of the wearable electronic device to tighten. In other examples, a user can provide input to the wearable electronic device to indicate the user's preference for the fit of the wearable electronic device to loosen.

Still further embodiments may include a configuration in which the instruction received in the course of operating methods described herein may be based on a user setting accessible to the wearable electronic device. For example, in some cases the wearable electronic device may access a secondary portable electronic device, a remote server, or a memory within the wearable electronic device itself to obtain an indication of a user's preference for the fit of the wearable electronic device. In some cases, a wearable electronic device can query a portable electronic device in communication therewith for a value corresponding to a user's preference for the tightness of the fit of the wearable electronic device. After obtaining the value from the portable electronic device, the wearable electronic device can provide the value to the tensioner in order to obtain or maintain the user's preferred fit.

Still further embodiments may include a configuration in which the instruction received in the course of operating methods described herein may be based on an output from a sensor in communication with the wearable electronic device. For example, in some embodiments, the wearable electronic device can include a tension sensor that can be configured to obtain a measurement or an approximation of the tightness of the band. In response to a tightness measurement above a selected threshold, the tension sensor can provide a signal to the wearable electronic device that the wearable electronic device can provide to the tensioner in order to loosen the fit of the band. Conversely, in response to a tightness measurement below a selected threshold, the tension sensor can provide a signal to the wearable electronic device that the wearable electronic device can provide to the tensioner in order to tighten the fit of the band. In still further examples, in response to a tightness measurement between selected thresholds, the tension sensor can provide a signal to the wearable electronic device that the wearable electronic device can use to determine that an adjustment of the fit of the wearable electronic device is not required.

Still further embodiments may include a configuration in which the instruction received in the course of operating methods described herein may be based on an operational state of the wearable electronic device. For example, if a wearable electronic device is operated in a fitness mode, the tensioner can tighten the band to fit more snugly about the user's wrist. In other examples, if a wearable electronic device is operated in a non-fitness mode, the tensioner can loosen the band.

Still further embodiments may include a configuration in which the instruction received in the course of operating methods described herein may be based on an operational state of a biometric sensor in communication with the wearable electronic device. For example, some biometric sensors may obtain more accurate or precise biometric data if said biometric sensor is positioned within a certain distance of a user's skin.

For example, a photoplethysmographic ("PPG") sensor may obtain more accurate and precise volumetric data if positioned in close proximity to a user's skin. In these embodiments, a biometric sensor in communication with the wearable electronic device may request an increase in tightness of the fit of the wearable electronic device prior to obtaining data. Similarly, after obtaining biometric data, the biometric sensor may request to return the fit of the wearable electronic device to the user's preferred fit.

In many cases, other embodiments described herein relate to methods of using a wearable electronic device having a dynamically adjustable fit. For example, some embodiments described herein relate to a method of soliciting attention (e.g., notifying by providing haptic output) of a user by adjusting the fit of a wearable electronic device secured to the user by a band. The method can begin by receiving an instruction to solicit attention of the user of some event, condition, data, or other information, and in response, actuate a tensioner coupled to the wearable electronic device to cause an increase in the tightness of the band. For example, a user may desire to be notified of an incoming email message. Upon receiving an indication that a new email message is received (or is being received), the wearable electronic device can increase the tightness of the band so as to quietly and discretely notify the user of the message.

In other cases, embodiments described herein relate to other methods of using a wearable electronic device having a dynamically adjustable fit. For example, a wearable electronic device can be used to provide haptic feedback for a cinema patron or a video game participant. In other examples, a wearable electronic device can be connected to home automation equipment. In such a case, a user may receive a notification of a knock on the front door via a tightening of the wearable electronic device. In another case, a user may receive a notification of a crying child in another room via a tightening of the wearable device.

In still other examples, a wearable electronic device having a dynamically adjustable fit can be used as an authentication device in a two-factor authentication system. For example, if a user wishes to access financial details hosted on a banking website, the banking website may require both the user's credentials and a verification of a number of tightening-loosening patterns sent to a wearable electronic device previously authenticated by the banking website. For example, a user can enter the user's credentials (e.g., username and password). Thereafter, the banking website can send a tactile pattern to a wearable electronic device previously authenticated by the banking website. In one example, a tactile pattern may be a series of five squeezes of the user's wrist (e.g., tighten and loosen in sequence). The user may thereafter enter "5" to gain access to the banking website.

In another embodiment, the wearable electronic device may be operated in a fitness/health tracking mode. In these embodiments, the wearable electronic device may tighten the fit of the band to count repetitions while the user is weight lifting. In another embodiment the wearable electronic device may tighten the fit of the band to notify a running user of certain distance intervals (e.g., every kilometer). In another embodiment, the wearable electronic device may notify a swimmer of an upcoming turn.

In still further embodiments, the wearable electronic device, operating as a navigation assistant, may tighten the fit of the band to notify a user to turn a certain direction. In these embodiments, the wearable electronic device can tighten a right portion of a band to indicate a right turn and can tighten a left portion of a band to indicate a left turn. In other embodiments, the wearable electronic device can tighten a band in order to wake a user from sleep. In another embodiment, the electronic device can tighten based on the user's geographic location. For example, if a user arrives at a fitness center, the wearable electronic device can tighten. Upon leaving the fitness center, the wearable electronic device can loosen.

Also described herein are methods of restraining a wearable electronic device secured by a strap to a user engaged in physical activity. For example, upon receiving an indication that the user may be engaged in physical activity (e.g., via output from a motion and/or acceleration sensor), a wearable electronic device can actuate a tensioner coupled to the wearable electronic device to increase the tightness of the strap. In one example, when a user begins a physical activity such as running, the wearable electronic device can respond by tightening around the user's wrist in order to prevent undesirable motion of the wearable electronic device about or along the user's wrist.

In many cases, other embodiments described herein relate to methods of using one or more wearable electronic devices having a dynamically adjustable fit as accessibility tools. For example, a user with sight impairment may operate a wearable electronic device as a means for discretely navigating an unknown environment. For example, a sight-impaired user may receive a notification via tightening of the wearable electronic device if the sight-impaired user is approaching an obstacle. In other examples, a hearing-impaired user may be notified when a loud sound is present of which the hearing-impaired user may not be aware (e.g., knock at a door). In other embodiments, a wearable electronic device such as described herein can provide compression therapy for a user with venous disorders. In some embodiments, a wearable electronic device such as described herein can be used as an emergency immobilization cuff, tightening around an injury to prevent movement or blood loss.

FIG. 1A depicts a perspective view of an example wearable electronic device loosely attached by a band to a user. In the illustrated embodiment, the wearable electronic device 100 is implemented as a portable electronic device that is worn on the wrist of a user 102. Other embodiments can implement the wearable electronic device differently. For example, the wearable electronic device can be a smart phone, a gaming device, a digital music player, a sports accessory device, a medical device, navigation assistant, accessibility device, a device that provides time and/or weather information, a health assistant, and other types of electronic device suitable for attaching to a user.

The wearable electronic device 100 includes a housing 104 and a display 106. In many examples, the display 106 may incorporate an input device configured to receive user input. For example, a user can provide input to the display 106 to indicate the user's intention to increase the tightness of the fit of the wearable device. In other examples, the user can provide a force input to the display 106, the magnitude of which can correspond to the magnitude of tightness increase in the fit the user desires to be implemented by the wearable electronic device 100.

The housing 104 can form an outer surface or partial outer surface and protective case for one or more internal components of the wearable electronic device 100. In the illustrated embodiment, the housing 104 is formed into a substantially rectangular shape, although this configuration is not required and other shapes are possible in other embodiments.

The housing 104 can be formed of one or more components operably connected together, such as a front piece and a back piece or a top clamshell and a bottom clamshell. Alternatively, the housing 104 can be formed of a single piece (e.g., uniform body or unibody).

The display 106 can be implemented with any suitable technology, including, but not limited to, a multi-touch sensing touchscreen that uses liquid crystal display (LCD) technology, light emitting diode (LED) technology, organic light-emitting display (OLED) technology, organic electroluminescence (OEL) technology, or another type of display technology. In many embodiments, the display 106 can have a resolution beyond 200 pixels per inch. In many embodiments, the display 106 can be disposed below a protective cover glass formed from a rigid and scratch resistant material such as ion-implanted glass, laminated glass, or sapphire.

As noted above, the display 106 can incorporate or be disposed proximate to an input sensor. For example, in some embodiments, the display 106 can also include one or more contact sensors to determine the position of one or more contact locations on a top surface of the display 106. For example, a contact sensor (such as a touch sensor or touch sensor array) can detect the location of one or more objects engaging the display 106, such as a stylus or a user's finger. In certain embodiments, a contact sensor can monitor an electrical property, such as conductance or capacitance. Upon detecting that the electrical property has changed at a location or area of the display 106, the contact sensor can report that an object is contacting the input surface at the specified location or area. In many cases, contact sensors may report the locations of all objects engaging the input surface. For example, a contact sensor may report two independent contact locations when a user positions two fingers on the display 106.

In some embodiments, the display 106 can also include one or more force-sensitive elements (not shown) to detect a magnitude of force applied to the top surface of the display 106. In some examples, the force-sensitive elements can be mechanically coupled to the underside of the display 106. In other examples, force-sensitive elements can be disposed around the perimeter of the display 106.

A force-sensitive element associated with the display 106 may be formed from a material or formed into a structure, such that upon application of a force (e.g., compression, expansion, tension, strain), one or more electrical properties of the material or structure can measurably change. Force-sensitive electrical properties can include conductance, accumulated charge, inductance, magnetic field strength, electrical field strength, capacitance, and so on. For example, a force-sensitive element formed from a piezoelectric material can accumulate charge in response to an applied force. In another example, a force-sensitive element can be formed as a structure (such as a number of layered materials) having a capacitance that measurably varies with force. In another example, a force-sensitive element can be formed from a strain-sensitive material that may measurably change in conductance (e.g., resistance) in response to a force. In these and some embodiments, a known relationship (e.g., linear, exponential, and so on) between the electrical property or properties and force applied can be used to determine an amount of force applied to display 106.

The wearable electronic device 100 can include within the housing 104 a processor, a memory, a power supply and/or battery, network communications, sensors, display screens, acoustic elements, input/output ports, haptic elements, digital and/or analog circuitry for performing and/or coordinating tasks of the wearable electronic device 100, and so on. In some examples, the wearable electronic device 100 can communicate with a separate electronic device via one or more proprietary and/or standardized wired and/or wireless interfaces. For simplicity of illustration, the wearable electronic device 100 is depicted in FIG. 1A without many of these elements, each of which may be included, partially, optionally, or entirely, within the housing 104.

The wearable electronic device 100 can be coupled to the user 102 via a band 108 that loops around the user's wrist. The band 108 can be formed from a compliant material, or into a compliant structure, that is configured to easily contour to a user's wrist, while retaining stiffness sufficient to maintain the position and orientation of the wearable electronic device on the user's wrist. The material selected for the band 108 may vary from embodiment to embodiment. For example, in certain cases, the band 108 can be formed from metal, such as a band formed into a metal mesh. In other embodiments, the band 108 can be formed from an organic material such as leather. In further examples, the band 108 can be formed from an inorganic material such as nylon. In still further embodiments, materials such as plastic, rubber, or other fibrous, organic, polymeric, or synthetic materials may be used.

As can be appreciated, the relative stiffness of a band can impact the tightness with which the band may be fit to a user's wrist. For example, the more flexible the band 108, the tighter the band should be secured to prevent the wearable electronic device 100 from sliding, rotating, or otherwise displacing on the user's wrist.

In some embodiments, the band 108 can be formed from a polymer, such as a fluoroelastomeric polymer, having a Shore durometer selected for having flexibility suitable for easily contouring to a user's wrists while maintaining sufficient stiffness to maintain support of the wearable electronic device 100 when attached to the wrist of user 102. For example, bands of certain embodiments may have a Shore A durometer ranging from 60 to 80 and/or a tensile strength greater than 12 MPa.

In some embodiments, a fluoroelastomeric polymer (or other suitable polymer) can be doped or treated with one or more other materials. For example, the polymer can be doped with an agent configured to provide the polymer with a selected color, odor, taste, hardness, elasticity, stiffness, reflectivity, refractive pattern, texture and so on. In other examples, the doping agent can confer other properties to the fluoroelastomeric polymer including, but not necessarily limited to, electrical conductivity and/or insulating properties, magnetic and/or diamagnetic properties, chemical resistance and/or reactivity properties, infrared and/or ultraviolet light absorption and/or reflectivity properties, visible light absorption and/or reflectivity properties, antimicrobial and/or antiviral properties, oleophobic and/or hydrophobic properties, thermal absorption properties, pest repellant properties, colorfast and/or anti-fade properties, deodorant properties, antistatic properties, medicinal properties, liquid exposure reactivity properties, low and/or high friction properties, hypoallergenic properties, and so on.

In some embodiments, one or more doping agents may be used. In further embodiments, the doping agents associated with one area of the band 108 may be different from the doping agents associated with another area of the bands. In one example, a band may have a low friction dopant added to the portion of a band that faces a user's wrist (e.g., bottom surface) while having a high reflectivity dopant added to the portion of the band that faces outwardly (e.g., top surface).

In some embodiments, one or more doping agents may be used to intentionally increase the elasticity of one or more portions of the band 108. For example, in some embodiments, a band 108 may include a compressible region having a greater elasticity than other regions of the band 108. This region can be configured to compress in response to an electrical signal from the wearable electronic device 100. In other examples, the compressible region can also be configured to expand in response to an electrical signal from the wearable electronic device 100.

In some examples, more than one compressible region can be used. In these cases, the several compressible regions of the band 108 can be independently, sequentially, or simultaneously compressed or expanded in response to an electrical signal from the wearable electronic device.

In some embodiments, as noted above, the compressible regions can be formed via doping the material selected for the band 108 with a dopant that increases the elasticity and/or compressibility of that selected region. In other examples, the compressible region(s) can be formed by hollowing a portion of the band 108. In other examples, the compressible region(s) can be formed by partially thinning a portion of the band 108. In still further examples, the compressible region(s) can be formed by causing macroscopic, microscopic, or nanoscopic pockets to form within the band 108. For example, in one embodiment, pockets of gas can be injected into a portion of the band. In another example, a portion of the band 108 can be intentionally weakened by microscopic perforations (e.g., via laser and/or water jet). In still further embodiments, a portion of the band can be formed as a foam, including many nano or microscopic cavities.

Other embodiments described herein include configurations in which the band 108 is formed from a non-compliant material into a compliant structure. For example, a metallic mesh can be used to form band 108. In other embodiments, the band can be formed by joining a number of metal links. In other embodiments, the band can be formed by joining a number of glass or crystal links.

In other embodiments, the band 108 can be formed form a combination of complaint and non-compliant materials.

In many examples, the band 108 can be removably coupled to the housing 104. For example, in certain embodiments, the band 108 can be at least partially looped around a watch pin that is configured to insert within lugs extending from the body of the housing 104. In other examples, the band 108 can be configured to slide within and be retained by two or more channels within external sidewalls of the housing 104. In other examples, the band 108 can be looped through and aperture in the housing 104. In other cases, the band 108 can be riveted, screwed, or otherwise attached to the housing 104 via one or more mechanical fasteners. In still further embodiments, additional removable couplings between the band 108 and the housing 104 are possible.

In other examples, the band 108 can be permanently coupled to the housing 104. For example, in some cases, the band 108 may be formed as an integral portion of the housing 104. In other cases, the band 108 can be rigidly adhered to the housing 104 via an adhesive. In still further embodiments, the band 108 can be welded, soldered, or chemically bonded to the housing 104. In other embodiments, additional permanent couplings between the band 108 and the housing 104 are possible.

As noted above, the housing 104 may be rigid and can be configured to provide structural support and impact resistance for electronic or mechanical components contained therein. A rigid housing is not necessarily required for all embodiments and, in some examples, the wearable electronic device 100 can have a housing may be flexible. Furthermore, although wearable electronic device housings are typically formed to take a rectangular shape, this is not required and other shapes are possible. For example, certain housings may take a circular shape.

In other embodiments, the wearable electronic device 100 can include one or more sensors (not shown) positioned on a bottom surface of the housing 104. Sensors utilized by the wearable electronic device 100 can vary from embodiment to embodiment. Suitable sensors can include temperature sensors, electrodermal sensors, blood pressure sensors, heart rate sensors, respiration rate sensors, oxygen saturation sensors, plethysmographic sensors, activity sensors, pedometers, blood glucose sensors, body weight sensors, body fat sensors, blood alcohol sensors, dietary sensors, and so on.

In many cases, sensors such as biometric sensors can collect certain health-related information non-invasively. For example, the wearable electronic device 100 can include a sensor that is configured to measure changes in (or an amount of) light reflected from a measurement site (e.g., wrist) of the user 102. In one embodiment, the biometric sensor such as a PPG sensor can include a light source for emitting light onto or into the wrist of the user 102 and an optical sensor to detect light exiting the wrist of the user 102. Light from the light source may be scattered, absorbed, and/or reflected throughout the measurement sight as a function of various physiological parameters or characteristics of the user 102. For example, the tissue of the wrist of the user 102 can scatter, absorb, or reflect light emitted by the light source differently depending on various physiological characteristics of the surface and subsurface of the user's wrist.

In many cases a PPG sensor can be used to detect a user's heart rate and blood oxygenation. For example, during each complete heartbeat, a user's subcutaneous tissue can distend and contract, alternatingly increasing and decreasing the light absorption capacity of the measurement site. In these embodiments, the optical sensor of the PPG can collect light exiting the measurement site and generate electrical signals corresponding to the collected light. Thereafter, the electrical signals can be conveyed as raw data to the wearable electronic device 100, which in turn can process the raw data into health data 110. The raw data can be based on information about the collected light, such as the chromaticity and/or luminance of the light. In some cases, the health data 110 can be shown on the display 106 as biometric feedback to the user 102.

However, certain sensors such as PPG sensors may be susceptible to noise associated with ambient light, surface conditions of the measurement site (e.g., cleanliness, hair, perspiration, etc.), proximity of the optical sensor and/or light source to the measurement site, and motion artifacts caused by the relative motion between the wearable electronic device 100 and the user 102. As a result, if the wearable electronic device 100 is not snugly fit to the user 102 (at least while the PPG sensor is obtaining a measurement), for example as illustrated in FIG. 1A, the health data 110 obtained from the sensor may be sub-optimal (e.g., insufficient or insignificant magnitude) as a direct result of the improper fit. Alternatively, if the wearable electronic device 100 is snugly fit to the user 102, for example as illustrated in FIG. 1B, the health data 110 obtained from the sensor may be of substantially improved quality, magnitude, and clarity.

Figure 1B:
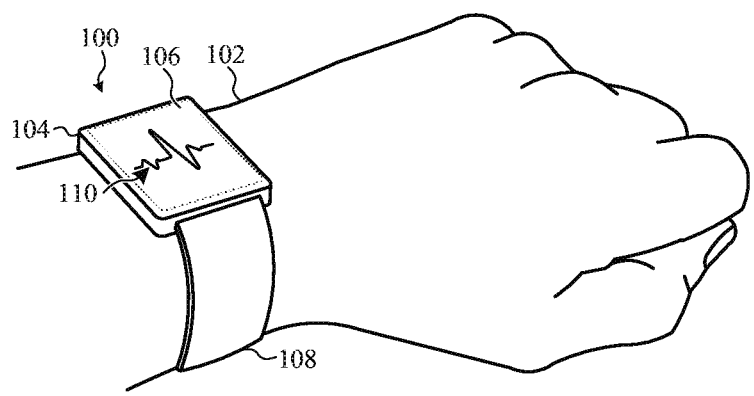
FIG. 1B depicts a perspective view of an example wearable electronic device tightly attached by a band to a user.

Although FIGS. 1A-1B are sequentially illustrated to show an improvement in the quality of health data 110 obtained by tightening the band 108, one can appreciate that in certain embodiments, the wearable electronic device 100 may dynamically resize the band 108 and/or the fit of the wearable electronic device 100 for reasons unrelated to sensor data quality.

For example, as mentioned above, a tensioner (not shown) can be coupled to the wearable electronic device 100. In some examples, the tensioner can be included within the housing 104. In other examples, the tensioner can be included within the band 108. In still further examples, a portion of the tensioner can be included within the housing 104 and a portion of the tensioner can be included within the band 108. In some examples, the tensioner can be coupled to the band 108 and to the housing 104. For example, the tensioner can take the form of a coupling and/or a lug by which the band 108 couples to the housing 104.

In many cases, a tensioner can be an analog, digital, or integrated circuit configured to apply an electrical signal to cause tension (either directly or indirectly) to be applied to, or relieved form, the band 108. In other cases, a tensioner can be a physical apparatus such as a motor, electromagnetic coil, or solenoid that can be actuated to cause tension (either directly or indirectly) to be applied to, or relieved form, the band 108.

For example, in some embodiments, a tensioner can apply an electrical current or voltage to an element that contracts or expands in the presence of an electrical current (e.g., piezoelectric materials, memory wire, electroactive polymers, etc.). In other examples, the tensioner can apply a current to an electromagnetic coil positioned proximate to a ferromagnetic material within the band. An increase in the current applied to the electromagnetic coil can cause a corresponding increase in the magnetic flux produced and, thus, an increase in the attractive force between the coil and the ferromagnetic material. In other embodiments, a permanent magnet can be disposed within the band such that the electromagnetic coil can be actuated to either repel or attract the permanent magnet. In still further examples, the tensioner can be implemented as a motor geared to a worm gear that either extends or retracts the band. In other examples, the tensioner can be implemented as a linear actuator. In other examples, the tensioner can be implemented as a fluid control system that is configured to increase or decrease the pressure and/or volume of a fluid within a particular portion of the band 108 or the housing 104. In other embodiments, the tensioner can be implemented as a combination of cooperating systems.

Figure 2A:
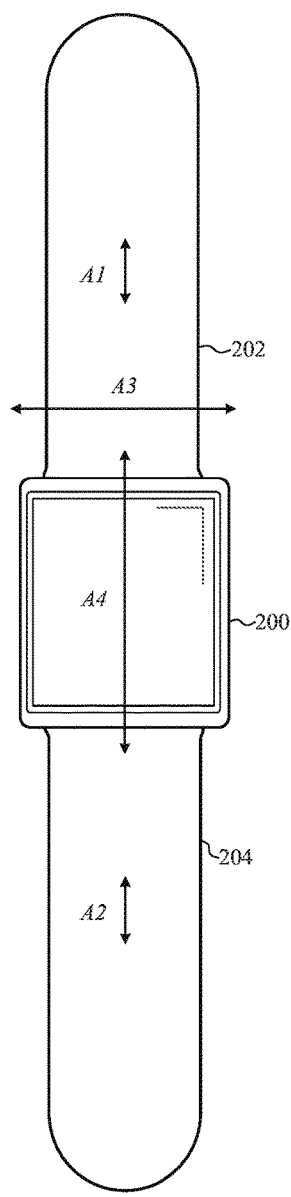
FIG. 2A depicts a top plan view of an example wearable electronic device with a two-piece band system for attaching to a user.

FIG. 2A depicts a top plan view of an example wearable electronic device 200 with a two-piece band system for attaching to a user. The wearable electronic device 200 can include a tensioner (not illustrated) in order to provide dynamic adjustment of the fit of the wearable electronic device 200. As with other embodiments described herein, the tensioner may alter the fit of the wearable electronic device 200 in a number of ways. For example, the tensioner can adjust one or more dimensions of a band coupled to the wearable electronic device. In another example, the tensioner can adjust a coupling between a band and the wearable electronic device. In another example the tensioner can adjust the position of the housing of the wearable electronic device relative to the band. In still other embodiments, other adjustments are possible.

In the illustrated embodiment, the wearable electronic device 200 is implemented as a portable electronic device that is adapted to be worn by a user, such as shown in FIGS. 1A-1B. Other embodiments can implement the wearable device differently. For example, the wearable device can be a smart phone, a gaming device, a digital music player, a sports accessory device, a medical device, a device that provides time and/or weather information, a health assistant, and other types of electronic device suitable for attaching to a user.

As with the embodiments depicted in FIGS. 1A-1B, the wearable electronic device 200 can include a housing and a display. In many examples, the display may incorporate an input device configured to receive touch input, force input, or other input from a user. The wearable electronic device 200 may also include one or more buttons or input ports (not shown). The housing can form a protective case for the internal components of the wearable electronic device 200. In the illustrated embodiment, the housing is formed into a substantially rectangular shape, although this configuration is not required.

Figure 2B:
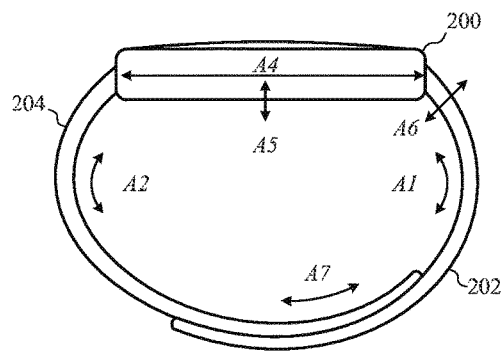
FIG. 2B depicts a side plan view of an example wearable electronic device with an overlapping two-piece band system for attaching to a user.
Figure 2C:
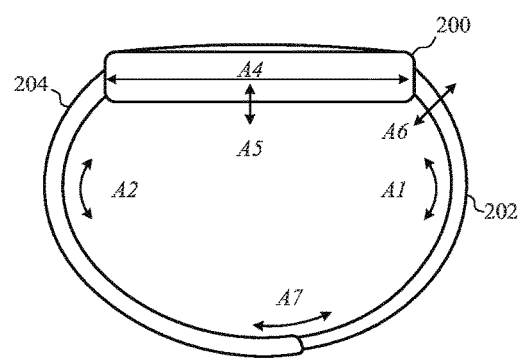
FIG. 2C depicts a side plan view of an example wearable electronic device with a mortise-tenon band system for attaching to a user.
Figure 2D:
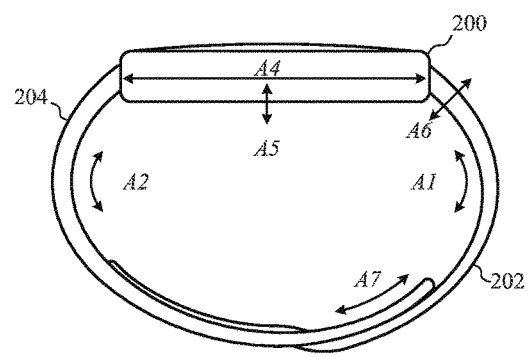
FIG. 2D depicts a side plan view of an example wearable electronic device with an interlacing band system for attaching to a user.

The wearable electronic device 200 can be permanently or removably attached to a band that is illustrated as a two-part band system including a first band 202 and a second band 204. In some embodiments, when attaching to a user's wrist, the first band 202 can be configured to overlap the second band 204, for example as depicted in FIG. 2B. In other embodiments, the first band 202 can be configured in a mortise-tenon relationship with the second band 204, such as depicted in FIG. 2C. In still further embodiments, the first band 202 can be configured to insert within an aperture of the second band 204 such that the first band 202 and the second band 204 interlace, such as depicted in FIG. 2D. In other embodiments, other relationships between the first band 202 and the second band 204 can be established.

The initial attachment between the first band 202 and the second band 204 (regardless whether the interaction is overlapping, interlacing, mortise-tenon or otherwise) is referred to herein as a "coarse" fit. A coarse fit may not provide users of the wearable electronic device 200 with a sufficiently many increments to find an optimally comfortable or preferred fit. For example, a coarse fit for the wearable electronic device 200 may be different when the user is operating the wearable electronic device 200 as a fitness/health tracker than when the same user is operating the wearable electronic device 200 as a conventional timekeeping device.

As with the embodiment depicted in FIGS. 1A-1B, the first band 202 and the second band 204 can each be formed from a compliant material or into a compliant structure that is configured to easily contour to a user's wrist, while retaining stiffness sufficient to maintain the position and orientation of the wearable electronic device on the user's wrist. In some embodiments, the first band 202 and the second band 204 may be formed from the same material, but this is not necessarily required. For example, in some embodiments the first band 202 can be formed from a leather material and the second band 204 can be formed from a metal material. In certain embodiments, the first band 202 and the second band 204 are each formed from a fluoroelastomeric polymer. In still further embodiments, materials such as plastic, rubber, or other fibrous, organic, polymeric, or synthetic materials may be used.

As noted above, the relative stiffness of the first band 202 and the second band 204 can impact the tightness with which the band may be fit to a user's wrist. Accordingly, in many embodiments, the wearable electronic device 200 may be configured to adjust one or more dimensions of the first band 202 or the second band 204. In other embodiments, the wearable electronic device 200 may be configured to adjust the coupling between the first band 202, the second band 204 and the housing of the wearable electronic device. In other embodiments, the wearable electronic device may be configured to adjust the housing itself.

For example, in some embodiments, the length of the first band 202 can be increased or decreased in order to adjust the fit of the wearable electronic device 200. In these embodiments, the shorter the length of the first band 202, the tighter the fit of the wearable electronic device 200 may be. Similarly, the longer the length of the first band 202, the looser the fit of the wearable electronic device 200 may be. Length adjustments to the first band 202 are shown in FIG. 2A with a bi-directional arrow labeled as adjustment A1.

In some embodiments, the length of the second band 204 can be increased or decreased in order to adjust the fit of the wearable electronic device 200. In these embodiments, the shorter the length of the second band 204, the tighter the fit of the wearable electronic device 200 may be. Similarly, the longer the length of the second band 204, the looser the fit of the wearable electronic device 200 may be. Length adjustments to the second band 204 are shown in FIG. 2A with a bi-directional arrow labeled as adjustment A2.

In some embodiments the adjustments A1, A2 can be carried out simultaneously, sequentially, or individually. For example, in some embodiments, the adjustment A1 can be carried out independent of the adjustment A2. In other words, the length of the first band 202 can be increased or decreased independent of any change in the length of the second band 204. In other embodiments, the adjustment A1 can be carried out to a greater degree than the adjustment A2. In other words, the length of the first band 202 can be increased or decreased by a greater amount than the any increase or decrease in the length of the second band 204.

In some embodiments, the width of the first band 202 can be increased or decreased in order to adjust the fit of the wearable electronic device 200. In these embodiments, the wider the first band 202, the tighter the fit of the wearable electronic device 200 may be. Similarly, the thinner the first band 202, the looser the fit of the wearable electronic device 200 may be. Width adjustments to the first band 202 are shown in FIG. 2A with a bi-directional arrow labeled as adjustment A3.

In some embodiments, the width of the second band 204 can be increased or decreased in order to adjust the fit of the wearable electronic device 200. In these embodiments, the wider the second band 204, the tighter the fit of the wearable electronic device 200 may be. Similarly, the thinner the second band 204, the looser the fit of the wearable electronic device 200 may be. For illustrative simplicity, width adjustments to the second band 204 are not illustrated in FIG. 2A.

In some embodiments width adjustments to the first band 202 and the second band 204 can be carried out simultaneously, sequentially, or individually. For example, in some embodiments, the adjustment A3 can be carried out independent of any width adjustment to the second band 204. In other embodiments, the adjustment A3 can be carried out to a greater degree any width adjustment to the second band 204.

In some embodiments, the relationship between the housing of the wearable electronic device 200 and the first band 202 and the second band 204 can be retracted or extended in order to adjust the fit of the wearable electronic device 200. In these embodiments, the more the first band 202 and/or the second band 204 are retracted into the housing of the wearable electronic device, the tighter the fit of the wearable electronic device 200 may be. Similarly, the more the first band 202 and/or the second band 204 are extended from the housing of the wearable electronic device 200, the looser the fit of the wearable electronic device 200 may be. Adjustments to the coupling between first band 202, the second band 204 and the housing of the wearable electronic device are shown in FIG. 2A with a bi-directional arrow labeled as adjustment A4.

FIG. 2B depicts a side plan view of an example wearable electronic device, such as shown in FIG. 2A, with an overlapping two-piece band system for attaching to a user. As with the embodiment depicted in FIG. 2A, the wearable electronic device 200 can include a tensioner to provide dynamic adjustment of the fit of the wearable electronic device 200. The wearable electronic device 200 can include a housing at that can be permanently or removably attached to a band that is illustrated as a two-part band system including a first band 202 and a second band 204.

As illustrated, the first band 202 and the second band 204 can be overlapped in order to form a closed loop around a user's wrist. In some examples, the first band 202 and the second band 204 can be affixed together with a traditional or conventional attachment mechanism. For example, in some embodiments, a buckling clasp can be used. In other examples a pin and eyelet attachment mechanism can be used.

Accordingly, and as with other embodiments described herein, the coarse fit of a wearable electronic device, such as the wearable electronic device 200 depicted in FIG. 2B can be adjusted by actuating a tensioner to adjust (or cause to be adjusted) one or more dimensions of the first band 202, the second band 204, the housing of the wearable electronic device 200, or the coupling between them. For example, as described above, a tensioner may be configured to carry out the adjustments A1, A2, A3 and/or A4.

In addition, in some embodiments, the height of the wearable electronic device 200 can be increased or decreased in order to adjust the fit of the wearable electronic device 200 when attached to a user. In these embodiments, the higher the housing of the wearable electronic device 200 is with respect to the user's wrist, the looser the fit of the wearable electronic device 200 may be. Similarly, the lower the housing of the wearable electronic device 200 is with respect to the user's wrist, the tighter the fit of the wearable electronic device 200 may be. Height adjustments to the housing of the wearable electronic device 200 are shown in FIG. 2B with a bi-directional arrow labeled as adjustment A5.

Furthermore, in some embodiments, the thickness of the first band 202 can be increased or decreased in order to adjust the fit of the wearable electronic device 200. In these embodiments, the thicker the first band 202, the shorter the first band 202, and thus the tighter the fit of the wearable electronic device 200 may be. Similarly, the thinner the first band 202, the looser the fit of the wearable electronic device 200 may be. Width adjustments to the first band 202 are shown in FIG. 2B with a bi-directional arrow labeled as adjustment A6.

Furthermore, in some embodiments, the thickness of the second band 204 can be increased or decreased in order to adjust the fit of the wearable electronic device 200. In these embodiments, the thicker the second band 204, the shorter the second band 204, and thus the tighter the fit of the wearable electronic device 200 may be. Similarly, the thinner the second band 204, the looser the fit of the wearable electronic device 200 may be. For illustrative simplicity, thickness adjustments to the second band 204 are not illustrated in FIG. 2B.

As with other adjustments described herein, in some embodiments, thickness adjustments to the first band 202 and the second band 204 can be carried out simultaneously, sequentially, or individually. For example, in some embodiments, the adjustment A6 can be carried out independent of any thickness adjustment to the second band 204. In other embodiments, the adjustment A6 can be carried out to a greater degree any thickness adjustment to the second band 204.

In addition, in some embodiments, the relative alignment of the first band 202 and the second band 204 can be changed in order to adjust the fit of the wearable electronic device 200. For example, the farther along the second band 204 the first band 202 is disposed, the tighter the fit of the wearable electronic device 200 may be. Relative alignment adjustments are shown in FIG. 2C with a bi-directional arrow labeled as adjustment A7.

FIG. 2C depicts a side plan view of an example wearable electronic device with a mortise-tenon band system for attaching to a user. As with the embodiment depicted in FIG. 2A, the wearable electronic device 200 can include a tensioner to provide dynamic adjustment of the fit of the wearable electronic device 200. The wearable electronic device 200 can include a housing at that can be permanently or removably attached to a band that is illustrated as a two-part band system including a first band 202 and a second band 204. As illustrated, the first band 202 can be inserted into a cavity opened within the second band 204 in order to form a coarse fit of closed loop around a user's wrist.

Accordingly, and as with other embodiments described herein, the coarse fit of a wearable electronic device, such as the wearable electronic device 200 depicted in FIG. 2C can be adjusted by actuating a tensioner to adjust (or cause to be adjusted) one or more dimensions of the first band 202, the second band 204, the housing of the wearable electronic device 200, or the coupling between them. For example, as described above, a tensioner may be configured to carry out the adjustments A1, A2, A3, A4, A5, A6, and/or A7.

FIG. 2D depicts a side plan view of an example wearable electronic device with an interlacing band system for attaching to a user. As with the embodiment depicted in FIG. 2A, the wearable electronic device 200 can include a tensioner to provide dynamic adjustment of the fit of the wearable electronic device 200. The wearable electronic device 200 can include a housing at that can be permanently or removably attached to a band that is illustrated as a two-part band system including a first band 202 and a second band 204. As illustrated, the first band 202 can be inserted into an aperture of the second band 204 in order to form a coarse fit of closed loop around a user's wrist.

In many examples, the first band 202 can include one or more sizing eyelets into which a pin associated with the second band 204 can be inserted. In many examples, more than one eyelet can be formed within the first band 202, distributed at uniform or semi-uniform intervals across the length of the band. In some examples, the eyelets may be distributed in a logarithmic or exponential distribution, or any other suitable distribution. In these embodiments, the distribution of the eyelets may be based, at least in part, on the average wrist size of the expected user. Some embodiments may not follow any mathematical distribution.

As illustrated, the second band 204 can include a concealment aperture (not visible) having a greater width than the first band 202. In some embodiments, the concealment aperture may be formed to have a width approximately equal to the width of the first band 202. The concealment aperture may be configured to receive the first band 202 through it, thereby concealing a portion of the first band 202 between the second band 204 and the user's wrist. In many embodiments, the concealment aperture is formed to have the shape of a rounded rectangle (e.g., "pill" shaped or "lozenge" shaped), although this shape is not required.

In many examples, the second band 204 can also include a pin (not illustrated) configured to be inserted in a selected eyelet of the first band 202. Upon insertion into the eyelet, the pin can resist unintended separation of the first band 202 and the second band 204. In many cases, the pin may be formed from metal, ceramic, or plastic and/or may include at least one surface finish configured to increase friction between the pin and the first band 202.

In many examples, the second band 204 can also incorporate a recessed guide bed (not visible) to receive and guide the inserted length of first band 202. In many cases, the guide bed can be longitudinally centered along the bottom surface of the second band 204. For these embodiments, the combined thickness of the overlapping portions of the sizing and second band 204 may be reduced. In addition, the guide bed may at least partially retain the inserted length of the first band 202 in place behind the second band 204.

To attach the portable electronic device around a user's wrist, the end of the first band 202 can be fed around the wrist and through the concealment aperture of the second band 204 so that the two bands interlace to form a closed loop. In many examples, the material selected for each band may have a low coefficient of friction such that the insertable end of the first band 202 can slide into the concealment aperture and against or past the user's skin without substantial resistance that might cause discomfort to the user. After insertion of the band-insertable end through the concealment aperture, the user can apply pressure to the first band 202 to push the first band 202 further along the guide bed of the second band 204 in order to adjust the tightness against the limb. When an acceptable tightness is reached, the user can push the pin of the second band 204 through the most proximate eyelet of the first band 202. In many embodiments, the process of inserting the band-insertable end and tightening the first band 202 and the second band 204s may be comfortably and conveniently accomplished with the user's free hand.

To detach the portable electronic device from the wrist, the pin can be withdrawn from the eyelet and the insertable end of the first band 202 can be withdrawn from the concealment aperture. The process of removing the insertable end and loosening the first band 202 and the second band 204 may be comfortably and conveniently accomplished with the user's free hand.

As with other embodiments described herein, the coarse fit of a wearable electronic device, such as the wearable electronic device 200 depicted in FIG. 2D can be adjusted by actuating a tensioner to adjust (or cause to be adjusted) one or more dimensions of the first band 202, the second band 204, the housing of the wearable electronic device 200, or the coupling between them. For example, as described above, a tensioner may be configured to carry out the adjustments A1, A2, A3, A4, A5, A6 and/or A7.

One can appreciate that although many embodiments are described herein with reference to two-part bands for attaching wearable electronic devices to users, that other bands are contemplated. For example, in some embodiments, a single-part band may be used. In other cases, a segmented band can be used.

Similarly, one may appreciate that the adjustments A1, A2, A3, A4, A5, A6 and/or A7 (and other adjustments) may apply equally or equivalently to other band and/or wearable electronic device embodiments described herein. More generally, it should be appreciated that the various examples and embodiments presented herein can apply equally or equivalently to many band and/or wearable device embodiments and no single embodiment, or adjustments thereto by a tensioner or the wearable electronic device itself, should be considered as limited to that single embodiment.

Figure 3A:
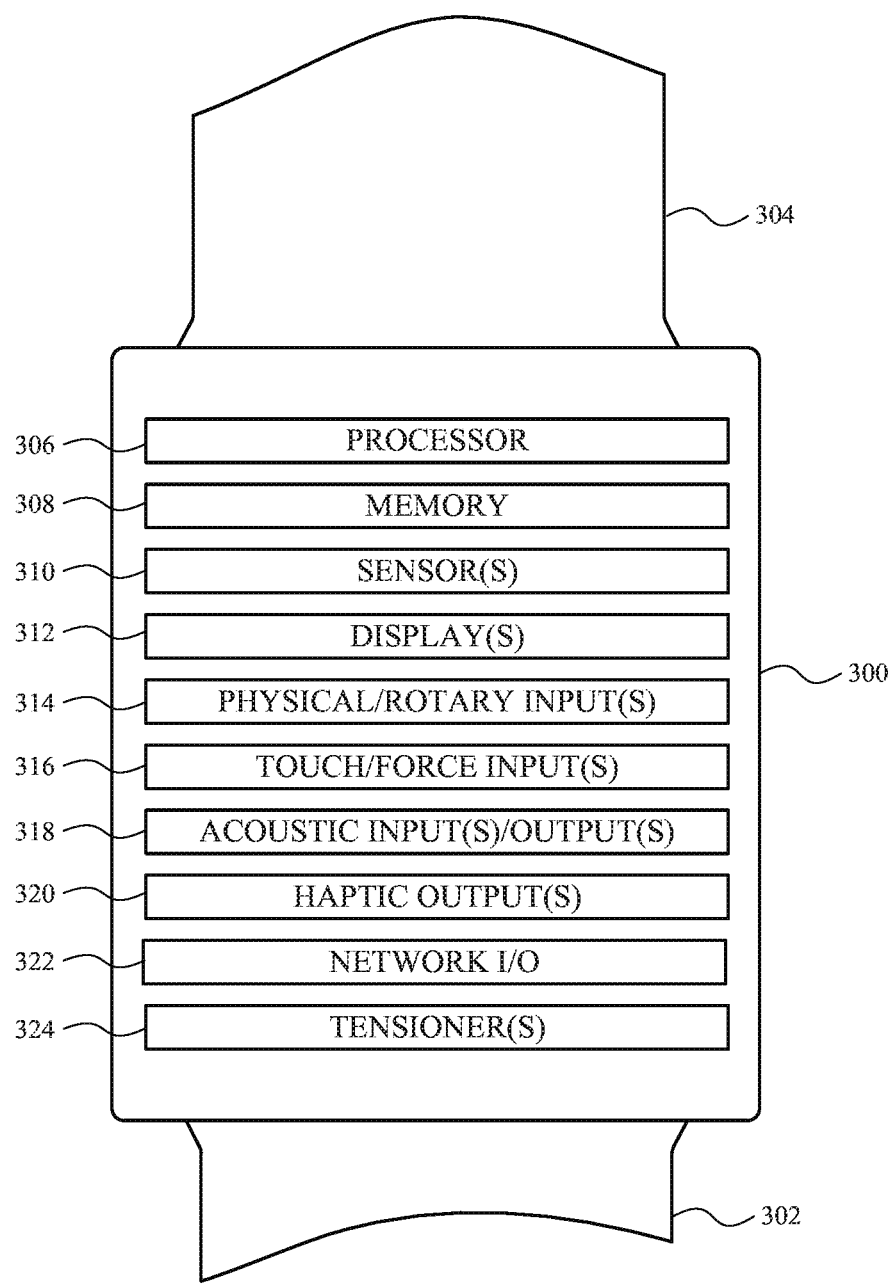
FIG. 3A depicts a simplified block diagram of a wearable electronic device.

FIG. 3A depicts a simplified block diagram of a wearable electronic device 300 configured to be coupled to a user by joining a first band 302 with a second band 304 about the user's wrist. The wearable electronic device 300 can one or more processing devices 306, memory 308, one or more input/output (I/O) devices or sensors 310 (e.g., biometric sensors, environmental sensors, etc.), one or more displays 312, one or more power source(s) (not shown), one or more physical and/or rotary input devices 314, one or more touch and/or force input device(s) 316, one or more acoustic input and/or output devices 318, one or more haptic output device(s) 320, one or more a network communication interface(s) 322, and one or more tensioner 324. Some embodiments can also include additional components.

The display 312 may provide an image or video output for the wearable electronic device 300. The display 312 may also provide an input surface for one or more input devices such as a touch sensing device 316, force sensing device, temperature sensing device, and/or a fingerprint sensor. The display 312 may be any size suitable for inclusion at least partially within the housing of the wearable electronic device 300 and may be positioned substantially anywhere on the wearable electronic device 300. In some embodiments, the display 312 can be protected by a cover glass formed from a scratch-resistant material (e.g., sapphire, zirconia, glass, and so on) that may form a substantially continuous external surface with the housing of the wearable electronic device 300.

The processing device(s) 306 can control or coordinate some or all of the operations of the wearable electronic device 300. The processing device 306 can communicate, either directly or indirectly with substantially all of the components of the wearable electronic device 300. For example, a system bus or signal line or other communication mechanisms can provide communication between the processing device 306, the memory 308, the I/O device(s) 310, the power source(s), the network communication interface 322, and/or the haptic output device 320.

The one or more processing devices 306 can be implemented as any electronic device capable of processing, receiving, or transmitting data or instructions. For example, the processing device(s) 306 can each be a microprocessor, a central processing unit (CPU), an application-specific integrated circuit (ASIC), a digital signal processor (DSP), or combinations of such devices. As described herein, the term "processing device" is meant to encompass a single processor or processing unit, multiple processors, multiple processing units, or other suitably configured computing element or elements.

The memory 308 can store electronic data that can be used by the wearable electronic device 300. For example, a memory can store electrical data or content such as, for example, audio and video files, documents and applications, device settings and user preferences, timing and control signals or data for the haptic output device 320, data structures or databases, and so on. The memory 308 can be configured as any type of memory. By way of example only, the memory can be implemented as random access memory, read-only memory, Flash memory, removable memory, or other types of storage elements, or combinations of such devices.

The one or more I/O device(s) 310 can transmit and/or receive data to and from a user or another electronic device. The I/O device(s) 310 can include a touch sensing input surface such as one or more buttons, one or more microphones or speakers, and/or one or more ports such as a microphone port.

The wearable electronic device 300 may also include one or more sensors 310 positioned substantially anywhere on the wearable electronic device 300. The sensor or sensors 310 may be configured to sense substantially any type of characteristic such as, but not limited to, images, pressure, light, touch, force, temperature, position, motion, and so on. For example, the sensor(s) 310 may be an image sensor, a temperature sensor, a light or optical sensor, an atmospheric pressure sensor, a humidity sensor, a magnet, a gyroscope, an accelerometer, and so on. In other examples, the wearable electronic device 300 may include one or more health sensors. In some examples, the health sensors can be disposed on a bottom surface of the housing of the wearable electronic device 300.

The power source can be implemented with any device capable of providing energy to the wearable electronic device 300. For example, the power source can be one or more batteries or rechargeable batteries, or a connection cable that connects the remote control device to another power source such as a wall outlet. In other examples, wireless power can be used.

The network communication interface 322 can facilitate transmission of data to or from other electronic devices across standardized or proprietary protocols. For example, a network communication interface can transmit electronic signals via a wireless and/or wired network connection. Examples of wireless and wired network connections include, but are not limited to, cellular, Wi-Fi, Bluetooth, infrared, and Ethernet.

The haptic output device 320 can be implemented as any suitable device configured to provide force feedback, vibratory feedback, tactile sensations, and the like. For example, in one embodiment, the haptic output device 320 may be implemented as a linear actuator configured to provide a punctuated haptic feedback, such as a tap or a knock.

As noted above, the wearable electronic device 300 can include a tensioner 324. In many cases, a tensioner can be an analog, digital, or integrated circuit configured to apply an electrical signal to cause tension (either directly or indirectly) to be applied to, or relieved form, the first band 302 and the second band 304. In other cases, a tensioner can be a physical apparatus such as a motor, electromagnetic coil, or solenoid that can be actuated to cause tension (either directly or indirectly) to be applied to, or relieved form, the first band 302 and/or the second band 304.

In response to a signal from the wearable electronic device, the tensioner can cause the first band 302 or the second band 304 to tighten and or loosen. In other embodiments, in response to a signal from the wearable electronic device 300, the tensioner can cause the housing of the wearable electronic device 300 to shift its position relative to the first band 302 or the second band 304.

Figure 3B:
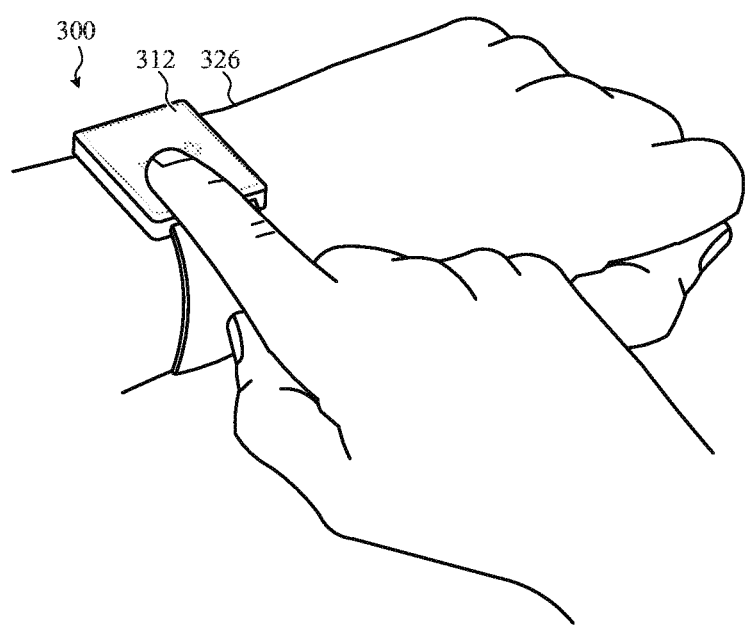
FIG. 3B depicts a perspective view of an example wearable electronic device depicting a user instructing the wearable electronic to adjust the fit of the band.

As noted above, the signal to change the fit of the wearable electronic device 300 can be received from any number of sources. For example, in certain embodiments, the signal can be received from secondary electronic device through the network communication interface 322. In other embodiments, the signal can be received as direct user input. For example, a user can provide input to the touch sensing device 316 of the wearable electronic device 300 to indicate to the wearable electronic device 300 and/or the tensioner 324 the user's desire for the fit of the device to change, either with increased tightness or decreased tightness. For example, FIG. 3B depicts in perspective view a user providing an indication to the wearable electronic device 300, via a display 312, to decrease the tightness of the band.

Figures 4A, 4B:
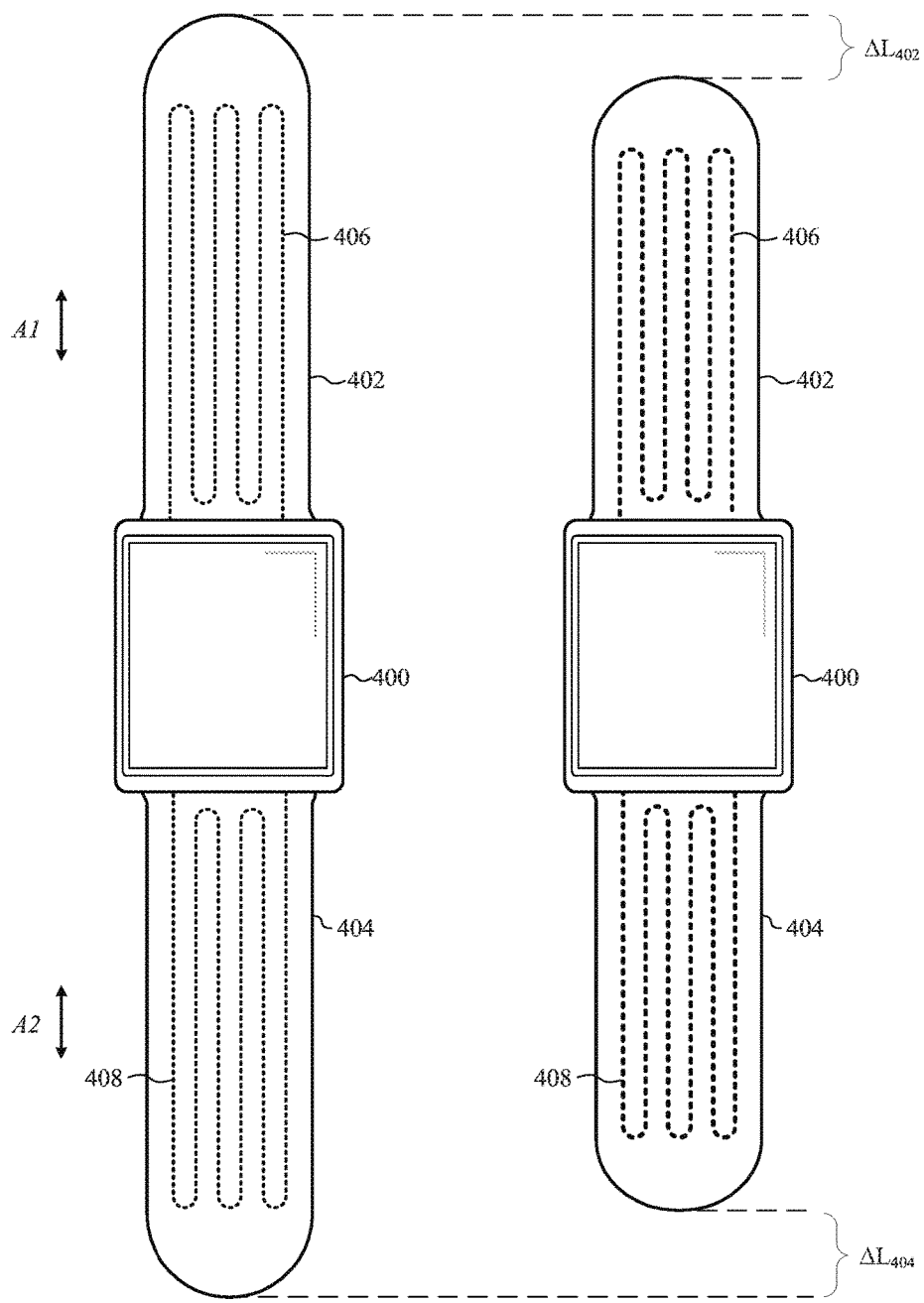
FIG. 4A depicts a top plan view of an example wearable electronic device with a two-piece band system configured to contract along its length in response to an electrical signal from a tensioner.
FIG. 4B depicts a top plan view of the example wearable electronic device of FIG. 4A, showing the two-piece band system in a contracted configuration.

FIG. 4A depicts a top plan view of an example wearable electronic device with a two-piece band system configured to contract along its length in response to an electrical signal from a tensioner. In many cases the tensioner can be coupled to one or more actuators that, in response to a signal from the tensioner, adjust the fit of the wearable electronic device.

The wearable electronic device 400 can include a housing at that can be permanently or removably attached to a band that is illustrated as a two-part band system including a first band 402 and a second band 404. In the illustrated embodiment, a first actuator 406 can be disposed within the first band 402 and a second actuator 408 can be disposed within a second band 404. Both the first actuator 406 and the second actuator 408 can be in electrical communication with a tensioner (not visible), which may be disposed within the housing of the wearable electronic device 400.

In the illustrated example, the first actuator 406 and the second actuator 408 can be formed in a longitudinal serpentine pattern and can be configured to contract or expand in response to an electrical signal from the tensioner. For example, in some embodiments, the first actuator 406 and the second actuator 408 can be formed from a shape memory wire such as Nitinol. In these embodiments, the tensioner can increase a current (or voltage) applied to the Nitinol in response to an instruction to increase the tightness of the band or can decrease a current (or voltage) applied to the Nitinol in response to an instruction to decrease the tightness of the band. In many cases, an increase in current applied to the Nitinol can cause the temperature of the Nitinol to increase, which can cause the Nitinol to contract.

In response to the increase or decrease in the length of the longitudinal and serpentine Nitinol, the band can experience an increase or decrease in length which, in turn, can cause an increase or decrease the tightness of the fit of the band, for example as illustrated in FIG. 4B. In this manner, the first actuator 406 and the second actuator 408 can achieve the adjustment A1 and/or the adjustment A2 discussed with respect to FIGS. 2A-2D.

In other embodiments, the first actuator 406 and the second actuator 408 can be formed from another shape-memory wire, such as a copper-based shape memory alloy. In other examples, another material can be used such as electroactive polymer (either dielectric or ionic). In response to an electrical signal from the tensioner, electroactive polymer can contract and/or expand to achieve the adjustments A1 and A2.

Although illustrated with a serpentine pattern, in other embodiments, other patterns can be used. For example, in other cases, a series of parallel actuators can be included within either or both the bands. In other examples, one or both of the actuators can be disposed along the entire length of one or both of the bands.

Figure 4C:
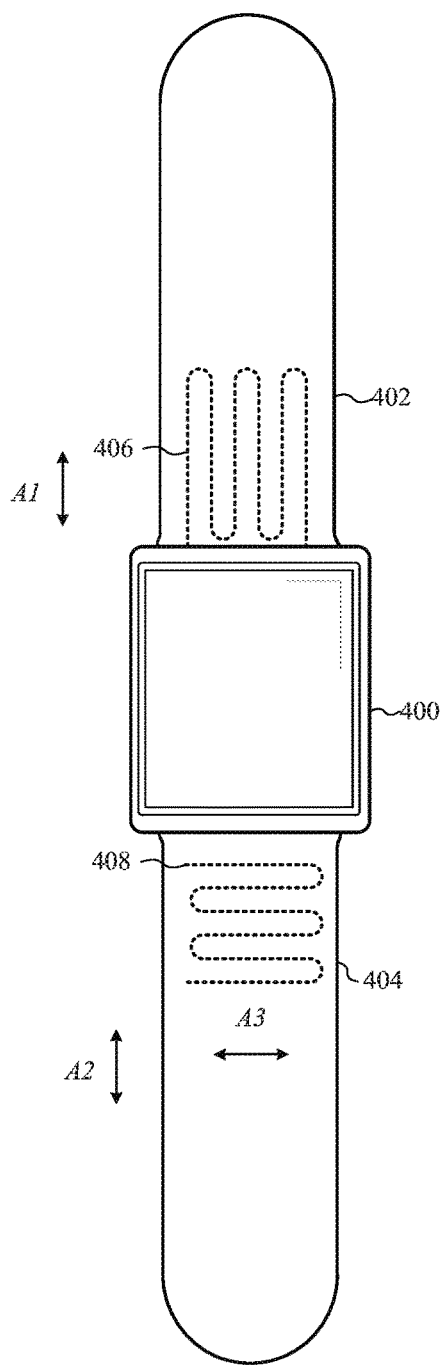
FIG. 4C depicts a top plan view of another example wearable electronic device with a two-piece band system configured to partially contract along its length in response to an electrical signal from a tensioner.

In other cases, the first actuator 406 and the second actuator 408 can be disposed only through a portion of the first band 402 and the second band 404. For example, FIG. 4C depicts the first actuator 406 as disposed only along a portion of the length of the first band 402. Although illustrated to abut the housing of the wearable electronic device 400, one can appreciate that the first actuator 406 can be positioned anywhere along the length of the first band 402. For example, in some embodiments, the first actuator 406 can be disposed in a middle portion of the first band 402. In other embodiments, the first actuator 406 can be disposed in an end portion of the first band 402. In still further embodiments, more than one actuator can be disposed within the first band 402. For example, one actuator can be placed within an end portion of the first band 402 and a second actuator can be positioned to abut the housing of the wearable electronic device 400.

In some embodiments, the first actuator 406 and the second actuator 408 can be insert molded into the first band 402 and the second band 404 respectively. In some cases, the first actuator 406 and the second actuator 408 can be insert molded closer to a bottom surface of the first band 402 and the second band 404. In other cases, the first actuator 406 and the second actuator 408 can be insert molded closer to a top surface of the first band 402 and the second band 404. In still further examples, the first actuator 406 and the second actuator 408 can be insert molded into the center of the first band 402 and the second band 404.

In other cases, the first actuator 406 and the second actuator 408 can be inserted into the first band 402 and the second band 404 after the molding of the first band 402 and the second band 404. For example, after molding, an incision path can be cut into the first band 402 and the second band 404 that is shaped to fit the shape of the first actuator 406 and the second actuator 408. In a subsequent manufacturing step, the first actuator 406 and the second actuator 408 can be inserted into the incision.

In other examples, the first actuator 406 and the second actuator 408 can be formed with selective placement of dopants during the formation of the first band 402 and the second band 404.

In other examples, the first actuator 406 and the second actuator 408 can be disposed on an exterior surface of the first band 402 and the second band 404. For example, in certain embodiments, the first actuator 406 and the second actuator 408 can be disposed around the perimeter of the first band 402 and the second band 404.

In still further examples, one or both of the first actuator 406 and the second actuator 408 can be disposed or formed along an axis that is not parallel to the length of the first band 402 or the second band 404. For example, as illustrated in FIG. 4C, the second actuator 408 can be disposed parallel to the width of the second band 404. In this example, contraction of the second actuator 408 can achieve an adjustment A3. In other words, contraction of the second actuator 408 can cause the width of the second band 404 to contract.

As may be appreciated, contraction of the width of the second band 404 can cause the second band 404 to lengthen. In other words, by achieving the adjustment A3, the adjustment A2 can also be achieved.

Figure 4D:
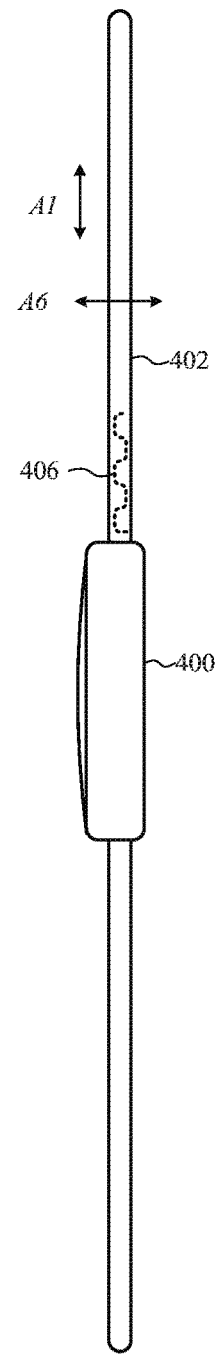
FIG. 4D depicts a side plan view of another example wearable electronic device with a two-piece band system configured to contract along its thickness in response to an electrical signal from a tensioner.

Similarly, and as depicted in the side plan view of FIG. 4D, some embodiments can dispose either or both the first actuator 406 and the second actuator 408 as a serpentine pattern through the thickness of the first band 402 or the second band 404. For example, as illustrated, the first actuator 406 can be disposed through the thickness of the first band 402. As may be appreciated, contraction of the thickness of the first band 402 can cause the first band 402 to lengthen. In other words, by achieving the adjustment A6, the adjustment A1 can also be achieved.

FIG. 5A depicts a top plan view of an example wearable electronic device with a two-piece band system configured to retract into the body of the wearable electronic device in response to an electrical signal from a tensioner. In many cases the tensioner can be coupled to one or more actuators that, in response to a signal from the tensioner, adjust the fit of the wearable electronic device.

The wearable electronic device 500 can include a housing at that can be permanently or removably attached to a band that is illustrated as a two-part band system including a first band 502 and a second band 504. In the illustrated embodiment, a first actuator 506 can be partially disposed within the first band 502 and partially disposed within the housing of the wearable electronic device. Similarly, a second actuator 508 can be partially disposed within a second band 504 and partially within the housing of the wearable electronic device. Both the first actuator 506 and the second actuator 508 can be in electrical communication with a tensioner (not visible), which may be disposed within the housing of the wearable electronic device 500.

In the illustrated example, the first actuator 506 and the second actuator 508 can be formed in a longitudinally-oriented serpentine pattern and can be configured to contract or expand in response to an electrical signal from the tensioner. For example, as with the embodiment depicted in FIGS. 4A-4D, the first actuator 506 and the second actuator 508 can be formed from a shape memory wire such as Nitinol.

In response to the increase or decrease in the length of the longitudinal and serpentine Nitinol, the band can experience an increase or decrease the tension with which the first band 502 and the second band 504 are coupled to the housing of the wearable electronic device 500, which, in turn, can cause an increase or decrease the tightness of the fit of the band. In this manner, the first actuator 506 and the second actuator 508 can achieve the adjustment A4.

In another embodiment, the tensioner can be connected to a coupling that joins the first band 502 and the second band 504 at one or more points to the housing of the wearable electronic device 500. In some examples, such as that depicted in FIG. 5B, the coupling can be a first lug 510 and a second lug 512, associated with the first band 502 and the second band 504 respectively, that each extend from the housing of the wearable electronic device 500. In such an embodiment, the tensioner can withdraw the first lug 510 and a second lug 512 into the housing of the wearable electronic device 500 by applying an electrical signal to the first actuator 506 and the second actuator 508 (shown in FIG. 5A).

In other examples, the first band 502 and the second band 504 can be configured to slide within (and be retained by) two or more channels within external sidewalls of the housing. In such an embodiment, such as that depicted in FIG. 5C, the tensioner can withdraw first channel 514 and a second channel 516, associated with the first band 502 and the second band 504 respectively, further into the housing of the wearable electronic device 500 by applying an electrical signal to the first actuator 506 and the second actuator 508. In another case, the tensioner can withdraw the portions of the first band 502 and the second band 504 that are inserted into the channels further into the housing of the wearable electronic device 500 by applying an electrical signal to the first actuator 506 and the second actuator 508.

In other examples, the first band 502 and the second band 504 can be looped through and aperture in the housing. In such an embodiment, the tensioner can withdraw the aperture further into the housing of the wearable electronic device 500 by applying an electrical signal to the first actuator 506 and the second actuator 508. In other cases, the first band 502 and the second band 504 can be riveted, screwed, or otherwise attached to the housing via one or more mechanical fasteners. In such an embodiment, the tensioner can withdraw the one or more mechanical fasteners further into the housing of the wearable electronic device 500 by applying an electrical signal to the first actuator 506 and the second actuator 508.

In other examples, the first band 502 and the second band 504 can be permanently coupled to the housing, such as depicted in FIG. 5D. For example, in some cases, the first band 502 and the second band 504 may be formed as an integral portion of the housing. In other cases, the first band 502 and the second band 504 can be rigidly adhered to the housing via a first adhesive 520 and a second adhesive 522, associated with the first band 502 and the second band 504 respectively. In still further embodiments, the first band 502 and the second band 504 can be welded, soldered, or chemically bonded to the housing. In other embodiments, additional permanent couplings between the first band 502 and the second band 504 and the housing of the wearable electronic device 500 are possible. In these embodiments, the tensioner can apply a withdrawing force to the first band 502 and the second band 504 such that the first band 502 and the second band 504 contract at their interface with the housing.

Figure 6A:
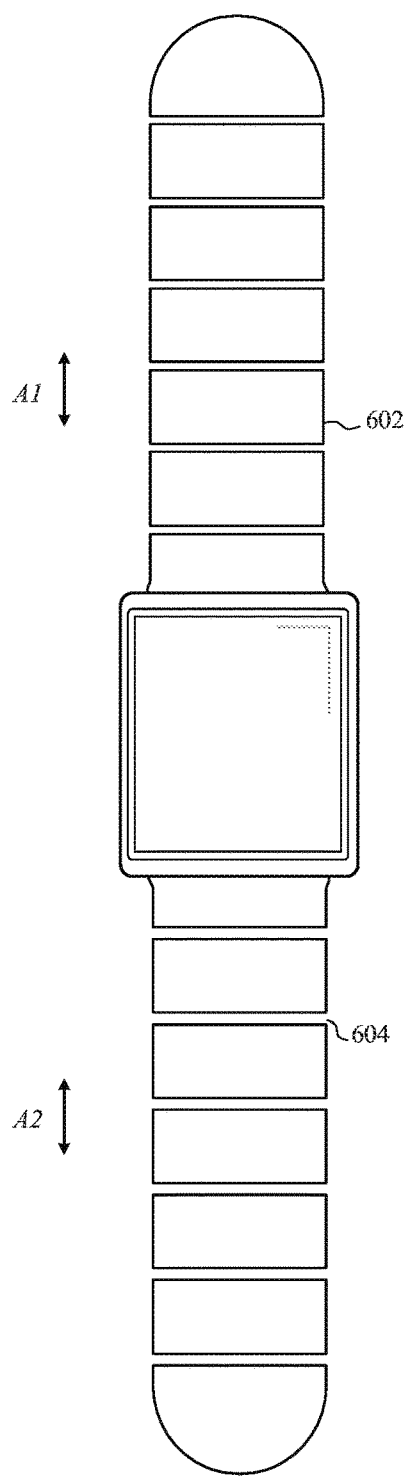
FIG. 6A depicts a top plan view of an example wearable electronic device with a segmented band system configured to contract along its length in response to an electrical signal from a tensioner.

FIG. 6A depicts a top plan view of an example wearable electronic device with a segmented band system configured to contract along its length in response to an electrical signal from a tensioner. In many cases the tensioner can be coupled to one or more actuators that, in response to a signal from the tensioner, adjust the fit of the wearable electronic device.

The wearable electronic device 600 can include a housing at that can be permanently or removably attached to a band that is illustrated as a two-part band system including a first band 602 and a second band 604. In the illustrated embodiment, the first band 602 and the second band 604 can each be formed as a group of metallic links. In other embodiments other materials can be used. For example, in some embodiments, glass, crystal, or rigid plastic can be used. In other examples, compliant materials can be used. In many cases, each link can be coupled to adjacent links via a hinging attachment. In other examples, each link can be coupled to adjacent links via an elasticated band.

In the illustrated embodiment, a first actuator 606 can be coupled to the first band 602. Similarly, a second actuator 608 coupled to the second band 604. Both the first actuator 606 and the second actuator 608 can be in electrical communication with a tensioner (not visible), which may be disposed within the housing of the wearable electronic device 600.

Figure 6B:
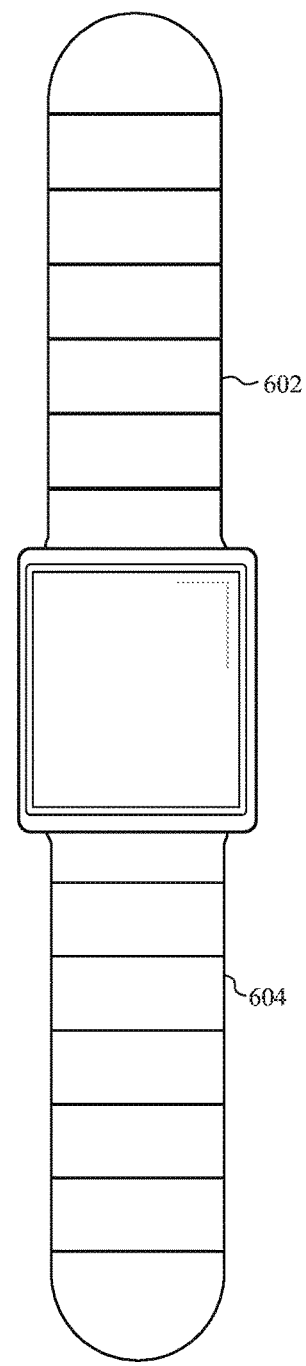
FIG. 6B depicts a top plan view of the example wearable electronic device of FIG. 6A, showing the segmented band system in a contracted configuration.

In the illustrated example, the first actuator 606 and the second actuator 608 can be configured contract or expand the first and/or second band in response to an electrical signal from the tensioner. For example, upon receiving a signal to contract (e.g., increase the tightness of the fit of the wearable electronic device 600, the links of each of the first band 602 and the second band 604 can be collapsed together, for example as shown in FIG. 6B In one embodiment, the first actuator 606 can be formed as a series of electromagnetic coils disposed within each link of the first band 602 and the second band 604. In this example, in response to an instruction to tighten the fit of the band, the tensioner can apply a current to each of the electromagnetic coils so that the band collapses into the configuration shown in FIG. 6B.

In another embodiment, as with the embodiment depicted in FIGS. 4A-4D, the first actuator 606 and the second actuator 608 can be formed from a shape memory wire such as Nitinol. The Nitinol wire can be fed through each of the links of each of the first band 602 and the second band 604. In some examples, the Nitinol can be fed through more than once, for example in a serpentine pattern. In this example, in response to an instruction to tighten the fit of the band, the tensioner can apply a current to the Nitinol wire so that the band collapses into the configuration shown in FIG. 6B.

In response to the increase or decrease in the length of the first band 602 and the second band 604, tightness of the fit of the wearable electronic device can respectively increase or decrease. In this manner, the first actuator 606 and the second actuator 608 can achieve the adjustment A1 and the adjustment A2.

FIG. 7A depicts a top plan view of an example wearable electronic device with a woven band system configured to contract along its length and/or width in response to an electrical signal from a tensioner. In many cases the tensioner can be coupled to one or more actuators that, in response to a signal from the tensioner, adjust the fit of the wearable electronic device.

The wearable electronic device 700 can include a housing at that can be permanently or removably attached to a band that is illustrated as a two-part band system including a first band 702 and a second band 704. In the illustrated embodiment, the first band 702 and a second band 704 can each be formed from a woven material. In many examples, a woven material can be made from a material that can be threaded, such as, but not limited to, plastic, rubber, nylon, cotton, or other fibrous, organic, polymeric, or synthetic materials. In many cases, a woven material can be formed by drawing a weft thread 708 through substantially parallel warp threads 710 in an patterned manner (e.g., alternating, alternating every other warp, alternating every third warp, etc.), for example as shown in the detail view of FIG. 7B. Nominally, one weft thread can be separated from adjacent weft threads by a distance 712 that defines the tightness of the woven material.

In the illustrated embodiment, a first actuator can be coupled to the first band 702. Similarly, a second actuator coupled to the second band 704. Both the first actuator 706 and the second actuator can be in electrical communication with a tensioner (not visible), which may be disposed within the housing of the wearable electronic device 700.

In the illustrated example, the first actuator and the second actuator can be configured contract or expand the first and/or second band in response to an electrical signal from the tensioner.

As with the embodiment depicted in FIGS. 4A-4D, the first actuator 706 and the second actuator can be formed from a shape memory wire such as Nitinol. In some cases the Nitinol wire can be threaded into the woven material forming the first band 702 and the second band 704. For example, in certain embodiments, the Nitinol wire can be one or more warps of the woven material. In another example, the Nitinol wire can be one or more wefts of the woven material. In this example, in response to an instruction to tighten the fit of the band, the tensioner can apply a current to the Nitinol wire so that the band collapses into the configuration shown in FIG. 7C. In other embodiments, the first actuator and the second actuator can be formed from another material, such as an electroactive polymer.

In response to the increase or decrease in the length of the first band 702 and the second band 704, tightness of the fit of the wearable electronic device can respectively increase or decrease. In this manner, the first actuator and the second actuator can achieve the adjustment A1 and the adjustment A2.

Figure 8A:
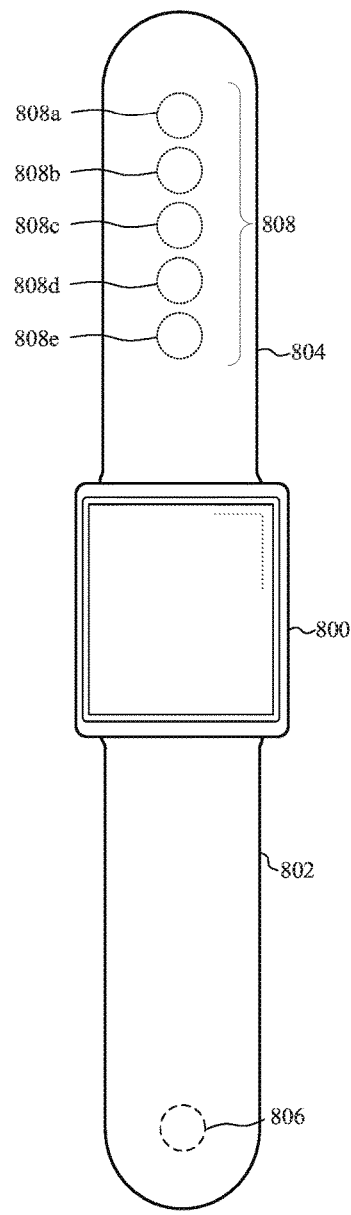
FIG. 8A depicts a top plan view of an example wearable electronic device with a two-part band system, each band configured to slide relative to the other band in response to an electrical signal from a tensioner.

FIG. 8A depicts a top plan view of an example wearable electronic device with a two-part band system, each band configured to slide relative to the other band in response to an electrical signal from a tensioner. In many cases the tensioner can be coupled to one or more actuators that, in response to a signal from the tensioner, adjust the fit of the wearable electronic device.

The wearable electronic device 800 can include a housing at that can be permanently or removably attached to a band that is illustrated as a two-part band system including a first band 802 and a second band 804. In the illustrated embodiment, a first actuator 806 can be partially disposed within the first band 802 and partially disposed within the housing of the wearable electronic device. Similarly, a second actuator 808 can be partially disposed within a second band 804 and partially within the housing of the wearable electronic device. Both the first actuator 806 and the second actuator 808 can be in electrical communication with a tensioner (not visible), which may be disposed within the housing of the wearable electronic device 800.

In the illustrated example, the first actuator 806 can be formed as a permanent magnet. The permanent magnet can be formed of any number of suitable magnetic materials. For example, in some embodiments, the first actuator 806 can be formed from rare earth metals. In other examples, the first actuator 806 can be formed as a ceramic magnet.

Figure 8B:
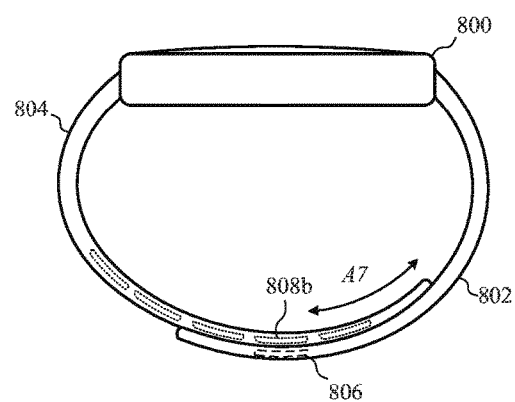
FIG. 8B depicts a side plan view of the example wearable electronic device of FIG. 8A.

In the illustrated example, the second actuator 808 can be formed as a series of electromagnetic coils, illustrated as the coils 806a-806e. Upon overlapping the first band 802 with the second band 804, the tensioner can send an electrical signal to one of the coils 806a-806e in order to attract the permanent magnetic the first actuator 806. For example, as shown in FIG. 8B, the coil 808b is activated by the tensioner so as to attract the permanent magnet of the first actuator 806.

Figure 8C:
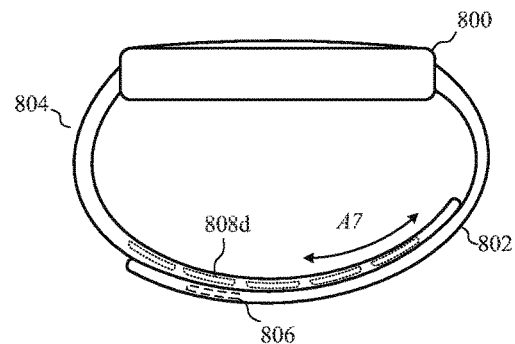
FIG. 8C depicts a side plan view of the example wearable electronic device of FIG. 8A in a contracted configuration.

In response to a signal to tighten the fit of the band, the tensioner can apply an electrical signal to one or more adjacent of the coils adjacent to the coil 808b, or whichever coil 808a-e was activated upon overlapping the first band 802 with the second band 804. For example, as shown in FIG. 8C, coil 808d can be activated so as to attract the permanent magnet of the first actuator 806.

In this manner, in response to the increase or decrease in the length of the first band 802 and the second band 804, tightness of the fit of the wearable electronic device can respectively increase or decrease. In this manner, the first actuator 806 and the second actuator 808 can achieve the adjustment A7.

Figure 9:
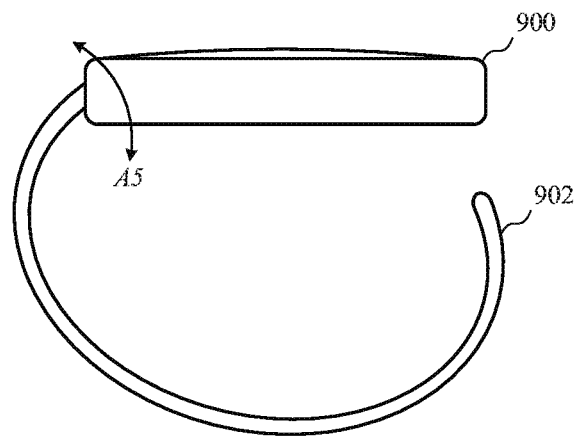
FIG. 9 depicts a side plan view of an example wearable electronic device with a bracelet-style band system configured to rotate the housing of the wearable electronic device toward or away from a user's wrist in response to an electrical signal from a tensioner.

FIG. 9 depicts a side plan view of an example wearable electronic device with a bracelet-style band system configured to rotate the housing of the wearable electronic device toward or away from a user's wrist in response to an electrical signal from a tensioner. In many cases the tensioner can be coupled to one or more actuators that, in response to a signal from the tensioner, adjust the fit of the wearable electronic device.

The wearable electronic device 900 can include a housing at that can be permanently or removably attached to a two-part band system including a rigid bracelet-style band 902. In the illustrated embodiment, the housing of the wearable electronic device 900 can be configured to rotate about a pivot point to which the rigid bracelet-style band 902 is coupled. For example, the wearable electronic device 900 can include an actuator (not shown) within the housing of the wearable electronic device 900 that can be electrically coupled to a tensioner (not shown) also disposed within the housing of the electronic device. In some embodiments, the actuator can be an electrical motor. In other examples, the actuator can be an electrical motor that, in other modes, is used to provide haptic feedback to the user. For example, the actuator may be a vibration motor.

In response to a signal to increase the tightness of the fit, the tensioner can cause the actuator to rotate the rigid bracelet-style band 902 relative to the housing of the wearable electronic device 900. By rotating the rigid bracelet-style band 902 toward the housing, the tightness of the fit can increase. By rotating the rigid bracelet-style band 902 away from the housing, the tightness of the fit can decrease.

In this manner, in response to the increase or decrease relative positioning of the rigid bracelet-style band 902 and the housing of the wearable electronic device 900, the tightness of the fit of the wearable electronic device can respectively increase or decrease. In this manner, the actuator can achieve the adjustment A5.

Figure 10:
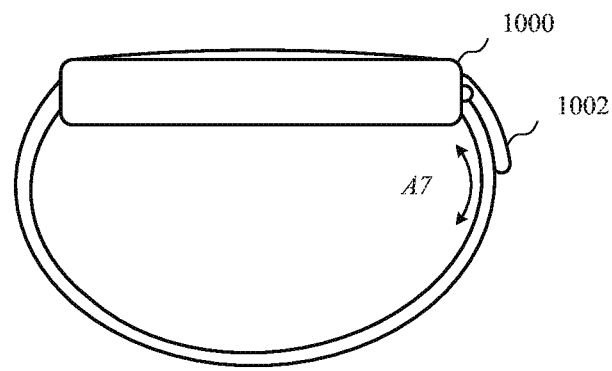
FIG. 10 depicts a side plan view of an example wearable electronic device with a loop-style band system configured to tighten or loosen the loop in response to an electrical signal from a tensioner.

FIG. 10 depicts a side plan view of an example wearable electronic device with a loop-style band system configured to tighten or loosen the loop in response to an electrical signal from a tensioner. In many cases the tensioner can be coupled to one or more actuators that, in response to a signal from the tensioner, adjust the fit of the wearable electronic device.

The wearable electronic device 1000 can include a housing at that can be permanently or removably attached to a two-part band system including a complaint loop-style band 1002. In the illustrated embodiment, the housing of the wearable electronic device 1000 can be configured to insert through about an aperture within the housing through which the complaint loop-style band 1002 can be inserted, and folded back on itself. In some examples, the complaint loop-style band 1002 can be formed from a metallic mesh. In some of these examples, the metallic mesh can be formed from a ferromagnetic material such as steel. In these examples, the complaint loop-style band 1002 can also include a permanent magnet, such as a bar magnet along the free end of the complaint loop-style band 1002. In this manner, after the complaint loop-style band 1002 is inserted and folded back upon itself, the permanent magnet can attract the complaint loop-style band 1002 itself in order to hold its position.

In some embodiments, the wearable electronic device 1000 can include an actuator (not shown) at least partially within the housing of the wearable electronic device 1000 that can be electrically coupled to a tensioner (not shown) also disposed within the housing of the electronic device. In some embodiments, the actuator can be an electrical motor that includes a gear or high-friction portion that is configured and oriented to feed the complaint loop-style band 1002 through the aperture in the housing in response to a signal from the tensioner. In some examples, the actuator can be an electrical motor that, in other modes, is used to provide haptic feedback to the user. For example, the actuator may be a vibration motor or a linear actuator.

In response to a signal to increase the tightness of the fit, the tensioner can cause the actuator to feed the complaint loop-style band 1002 through the aperture in the housing of the wearable electronic device 1000. By feeding the complaint loop-style band 1002 through the aperture in the housing, the tightness of the fit can be increased or decreased, depending upon the direction of the feed.

In this manner, in response to the increase or decrease relative positioning of the complaint loop-style band 1002 and the housing of the wearable electronic device 1000, the tightness of the fit of the wearable electronic device can respectively increase or decrease. In this manner, the actuator can achieve the adjustment A5.

Figure 11A:
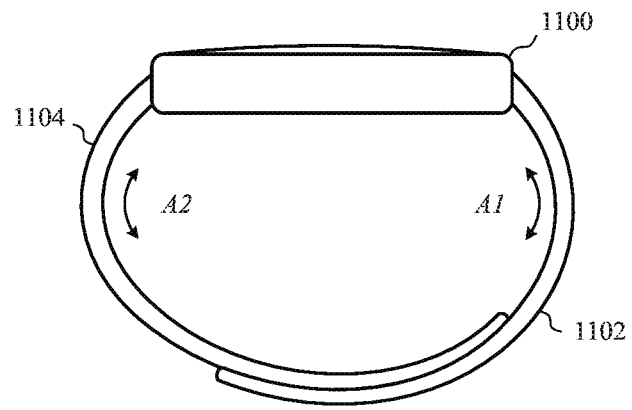
FIG. 11A depicts a side plan view of an example wearable electronic device with a bladder-style band system configured to increase or decrease pressure within one or more bladders in response to an electrical signal from a tensioner.

FIG. 11A depicts a side plan view of an example wearable electronic device with a bladder-style band system configured to increase or decrease pressure within one or more bladders in response to an electrical signal from a tensioner. In many cases the tensioner can be coupled to one or more actuators that, in response to a signal from the tensioner, adjust the fit of the wearable electronic device.

The wearable electronic device 1100 can include a housing at that can be permanently or removably attached to a band that is illustrated as a two-part band system including a first band 1102 and a second band 1104. In the illustrated embodiment, the first band 1102 and a second band 1104 can each be formed with one or more bladders that are in communication with an actuator such as a pump that is disposed within the housing of the wearable electronic device 1100.

In the illustrated embodiment, a first actuator can be associated with the first band 1102. Similarly, a second actuator can be associated with the second band 1104. Both the first actuator and the second actuator can be in electrical communication with a tensioner (not visible), which may be disposed within the housing of the wearable electronic device 1100.

Figure 11B:
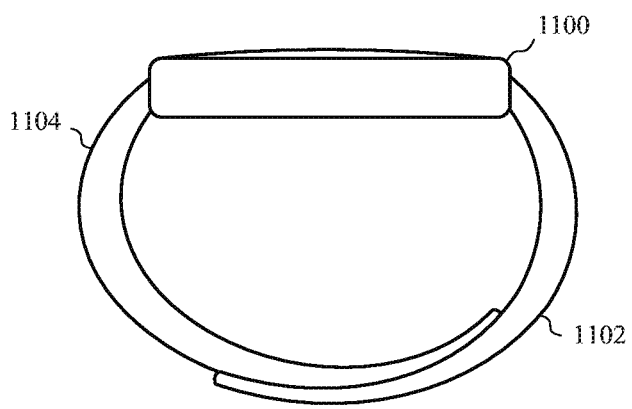
FIG. 11B depicts a side plan view of the example wearable electronic device of FIG. 11A, depicting inflated bladders.

The tensioner may be configured to control the pressure applied by the actuators to a fluid in communication with the bladders. In some cases the fluid can be a gas or a liquid. For example, in some embodiments, air can be used as the fluid in communication with the bladder. In other cases, a liquid with a low viscosity such as oil or water can be used as the fluid in communication with the bladder. In these embodiments, the tensioner can increase the pressure applied by the pump to the fluid in response to an instruction to increase the tightness of the band or can decrease the pressure applied by the pump in response to an instruction to decrease the tightness of the band. In response to the increase or decrease in pressure, the bladder can experience an increase or decrease in volume, which, in turn, increases or decreases the tightness of the band, for example as depicted in FIG. 11B.

In response to the increase or decrease in the length of the first band 1102 and the second band 1104, tightness of the fit of the wearable electronic device can respectively increase or decrease. In this manner, the first actuator and the second actuator can achieve the adjustment A1 and the adjustment A2.

Figure 12A:
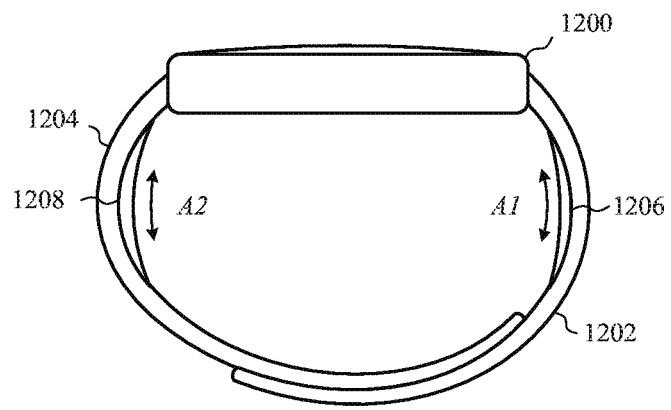
FIG. 12A depicts a side plan view of an example wearable electronic device with another bladder-style band system configured to increase or decrease pressure within one or more bladders in response to an electrical signal from a tensioner.

FIG. 12A depicts a side plan view of an example wearable electronic device with another bladder-style band system configured to increase or decrease pressure within one or more bladders in response to an electrical signal from a tensioner. In many cases the tensioner can be coupled to one or more actuators that, in response to a signal from the tensioner, adjust the fit of the wearable electronic device.

The wearable electronic device 1200 can include a housing at that can be permanently or removably attached to a band that is illustrated as a two-part band system including a first band 1202 and a second band 1204. In the illustrated embodiment, the first band 1202 and a second band 1204 can each be formed with a first bladder 1206 and a second bladder 1208, respectively, that each are in communication with an actuator such as a pump that is disposed within the housing of the wearable electronic device 1200.

In the illustrated embodiment, a first actuator can be associated with the first band 1202. Similarly, a second actuator can be associated with the second band 1204. Both the first actuator and the second actuator can be in electrical communication with a tensioner (not visible), which may be disposed within the housing of the wearable electronic device 1200.

Figure 12B:
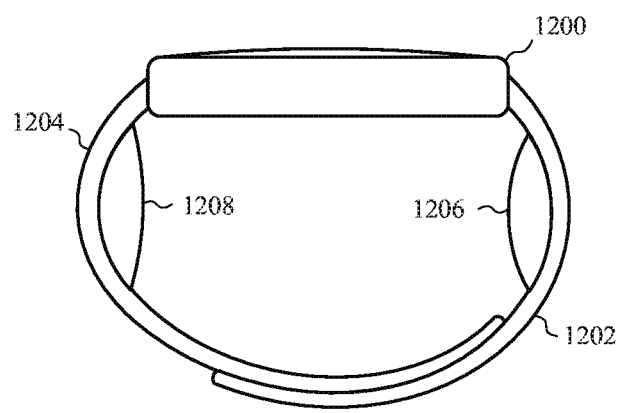
FIG. 12B depicts a side plan view of the example wearable electronic device of FIG. 12A, depicting inflated bladders.

The tensioner may be configured to control the pressure applied by the actuators to a fluid in communication with the first bladder 1206 and a second bladder 1208. As with the embodiment depicted in FIGS. 11A-11B, the fluid can be any suitable fluid. In response to a request to increase or decrease the tightness of the fit of the band of the wearable electronic device 1200, the tensioner can cause the actuators to increase or decrease the pressure of the first bladder 1206 and a second bladder 1208. In response to the increase or decrease in pressure, the first bladder 1206 and a second bladder 1208 can experience an increase or decrease in volume, which, in turn, increases or decreases the tightness of the band, for example as depicted in FIG. 12B.

In response to the increase or decrease in the length of the first band 1202 and the second band 1204, tightness of the fit of the wearable electronic device can respectively increase or decrease. In this manner, the first actuator and the second actuator can achieve the adjustment A1 and the adjustment A2.

Figure 13A:
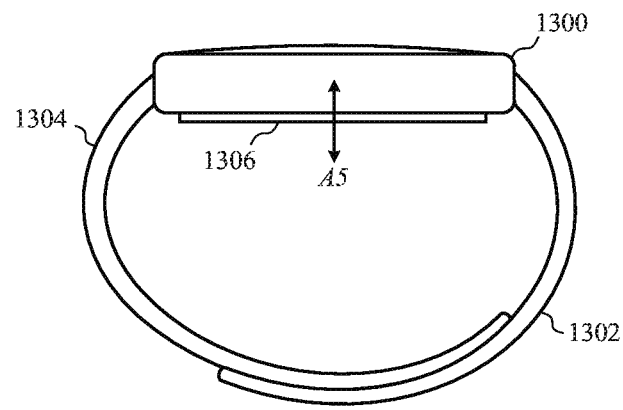
FIG. 13A depicts a side plan view of an example wearable electronic device with an extendable housing portion configured to extend toward or retract from a user's skin in response to an electrical signal from a tensioner.

FIG. 13A depicts a side plan view of an example wearable electronic device with an extendable housing portion configured to extend toward or retract from a user's skin in response to an electrical signal from a tensioner. In many cases the tensioner can be coupled to one or more actuators that, in response to a signal from the tensioner, adjust the fit of the wearable electronic device.

The wearable electronic device 1300 can include a housing at that can be permanently or removably attached to a band that is illustrated as a two-part band system including a first band 1302 and a second band 1304. In the illustrated embodiment, the housing of the wearable electronic device 1300 can include an extendable portion that can be configured to extend from a bottom surface of the housing toward the user's wrist.

In the illustrated embodiment, an actuator 1306 can be configured to extend the extendable portion. The actuator can be in electrical communication with a tensioner (not visible), which may be disposed within the housing of the wearable electronic device 1300.

In this embodiment, the actuator 1306 can cause the extendable portion of the housing of the wearable electronic device 1300 to extend toward or retract from the user's skin. For example, in certain embodiments the extendable portion can extend toward a user's wrist (see, e.g., FIG. 13B) or, in other examples, the extendable portion can retract from the user's wrist. In such an embodiment, the tensioner can cause the actuator 1306 to extend the extendable portion in response to an instruction to increase the tightness of the band or the tensioner can cause the actuator 1306 to withdraw the extendable portion into the housing of the wearable electronic device in response to an instruction to decrease the tightness of the band.

In some embodiments, the extendable portion can be formed from a material that contracts or expands in the presence of an electrical current (e.g., piezoelectric materials, memory wire, electroactive polymers, etc.). In other examples, the extendable portion can be formed as an electromagnetic coil positioned proximate to a permanent magnet (or other electromagnetic coil) coupled to a bottom surface of the housing of the wearable electronic device 1300. An increase in the current applied to the electromagnetic coil can cause a corresponding increase in the magnetic flux produced and, thus, an increase in the attractive or repulsive force between the coil and the permanent magnetic material.

In still further examples, the extendable portion can be extended with a motor geared to a worm gear that either extends or retracts the extendable portion. In other examples, the extendable portion can be implemented as a linear actuator that extends or retracts the extendable portion. In other examples, the extendable portion can be implemented as a fluid pressure control system such as a pump that is configured to increase or decrease the pressure and/or volume of a fluid that then causes the extendable portion of the housing to extend or contract. In some examples, the extendable portion can be mechanically biased by a spring. In some cases, the bias can cause the extendable portion to be biased inwardly, in other cases, the bias spring can cause the extendable portion to be biased outwardly.

Furthermore, although illustrated as a large portion of the bottom surface of the wearable electronic device 1300, one can appreciate that in other embodiments, smaller extendable portions are possible. For example, in certain embodiments, an optical biometric sensor coupled to the bottom surface of the housing of the wearable device (e.g., PPG sensor) may require one or more transparent or semi-transparent lenses such that optical components of the sensor can be exposed to conditions external to the housing of the wearable electronic device 1300. In some embodiments, these lenses can be extendable portions. For example, one or more sensor lenses can extend or withdraw from contact with the user's skin.

In this manner, in response to the increase or decrease in the height of the housing relative to the first band 1302 and the second band 1304, tightness of the fit of the wearable electronic device can respectively increase or decrease. In this manner, the actuator can achieve the adjustment A5.

Figure 14A:
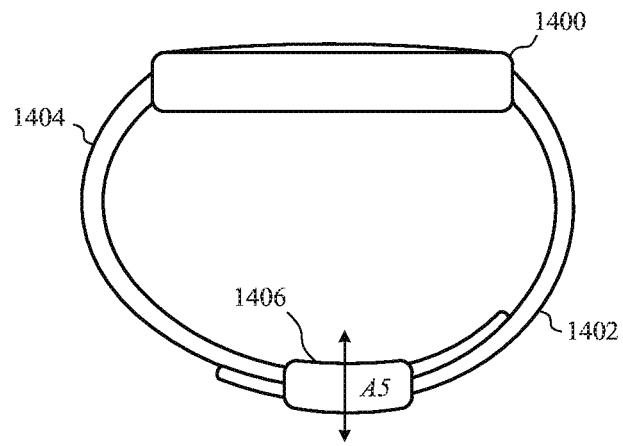
FIG. 14A depicts a side plan view of an example wearable electronic device with an extendable buckle portion configured to extend toward or retract from a user's skin in response to an electrical signal from a tensioner.

FIG. 14A depicts a side plan view of an example wearable electronic device with an extendable buckle portion configured to extend toward or retract from a user's skin in response to an electrical signal from a tensioner. In many cases the tensioner can be coupled to one or more actuators that, in response to a signal from the tensioner, adjust the fit of the wearable electronic device.

The wearable electronic device 1400 can include a housing at that can be permanently or removably attached to a band that is illustrated as a two-part band system including a first band 1402 and a second band 1404. The first band 1402 and the second band 1404 can be joined by a buckle that can include an extendable portion that can be configured to extend from a top surface of the buckle toward the user's wrist.

In the illustrated embodiment, an actuator 1406 can be configured to extend the extendable portion. The actuator can be in electrical communication, either wireless or wired, with a tensioner (not visible), which may be disposed within the housing of the wearable electronic device 1400.

Figure 14B:
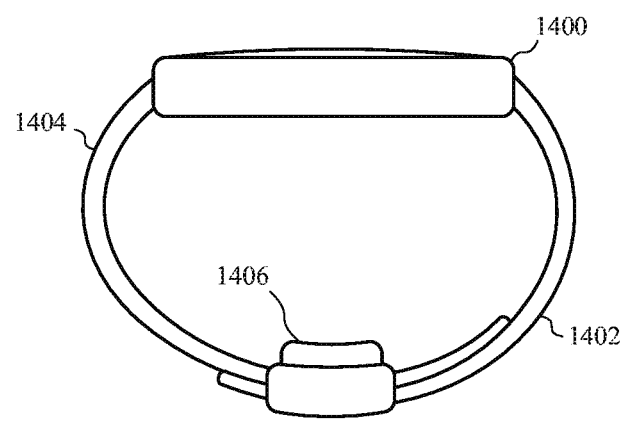
FIG. 14B depicts a side plan view of the example wearable electronic device of FIG. 14A depicting an extended buckle portion.

In this embodiment, the actuator 1406 can cause the extendable portion of the buckle to extend toward or retract from the user's skin. For example, in certain embodiments the extendable portion can extend toward a user's wrist (see, e.g., FIG. 14B) or, in other examples, the extendable portion can retract from the user's wrist. In such an embodiment, the tensioner can cause the actuator 1406 to extend the extendable portion in response to an instruction to increase the tightness of the band or the tensioner can cause the actuator 1406 to withdraw the extendable portion into the buckle in response to an instruction to decrease the tightness of the band.

Figure 13B:
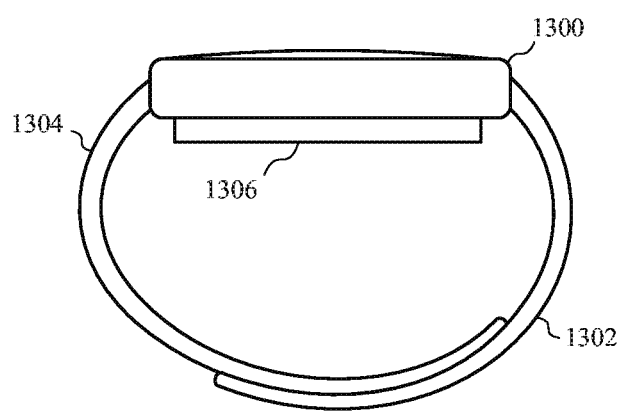
FIG. 13B depicts a side plan view of the example wearable electronic device of FIG. 13A, depicting an extended housing portion.

As with the extendable portion described with respect to the embodiment depicted in FIGS. 13A-13B, the extendable portion of the buckle can be implemented using piezoelectric materials, electroactive polymers, pumps and fluids, electromagnetic attraction and repulsion, and so on.

In this manner, in response to the increase or decrease in the height of the housing relative to the first band 1402 and the second band 1404, tightness of the fit of the wearable electronic device can respectively increase or decrease. In this manner, the actuator 1406 can achieve the adjustment A5.

Figure 15A:
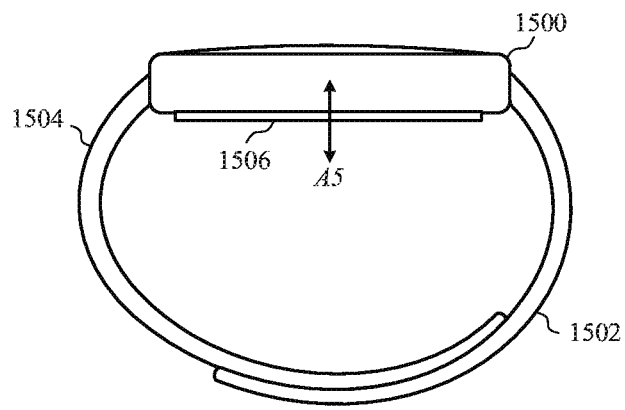
FIG. 15A depicts a side plan view of an example wearable electronic device with another extendable housing portion configured to extend toward or retract from a user's skin in response to an electrical signal from a tensioner.

FIG. 15A depicts a side plan view of an example wearable electronic device with another extendable housing portion configured to extend toward or retract from a user's skin in response to an electrical signal from a tensioner. In many cases the tensioner can be coupled to one or more actuators that, in response to a signal from the tensioner, adjust the fit of the wearable electronic device.

The wearable electronic device 1500 can include a housing at that can be permanently or removably attached to a band that is illustrated as a two-part band system including a first band 1502 and a second band 1504. In the illustrated embodiment, the housing of the wearable electronic device 1500 can include a deformable portion that can be configured to deform away from a bottom surface of the housing toward the user's wrist.

In the illustrated embodiment, an actuator 1506 can be configured to deform the deformable portion. The actuator can be in electrical communication with a tensioner (not visible), which may be disposed within the housing of the wearable electronic device 1500.

Figure 15B:
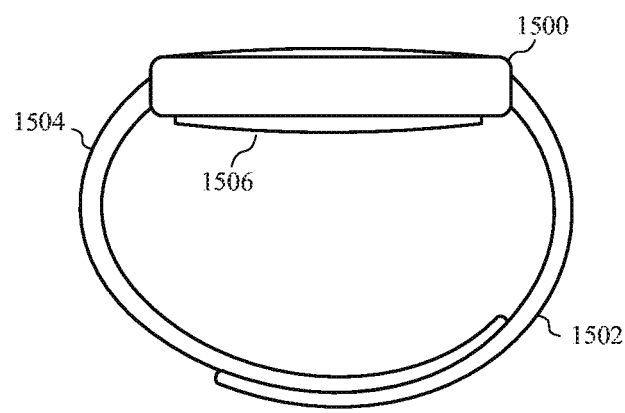
FIG. 15B depicts a side plan view of the example wearable electronic device of FIG. 15A, depicting an extended housing portion.

In this embodiment, the actuator 1506 can cause the deformable portion of the housing of the wearable electronic device 1500 to deform toward or deform away from the user's skin. For example, in certain embodiments the deformable portion can deform toward a user's wrist (see, e.g., FIG. 15B) or, in other examples, the deformable portion can deform away from the user's wrist. In such an embodiment, the tensioner can cause the actuator 1506 to deform the deformable portion in response to an instruction to increase the tightness of the band or the tensioner can cause the actuator 1506 to withdraw the deformable portion toward the housing of the wearable electronic device in response to an instruction to decrease the tightness of the band.

In addition, although the deformable portion is illustrated with an arcuate deformation, such a deformation is not required. For example, in other embodiments, other deformations are possible.

As with the deformable portion described with respect to the embodiment depicted in FIGS. 13A-13B, the deformable portion of the buckle can be implemented using piezoelectric materials, electroactive polymers, pumps and fluids, electromagnetic attraction and repulsion, and so on.

In this manner, in response to the increase or decrease in the height of the housing relative to the first band 1502 and the second band 1504, tightness of the fit of the wearable electronic device can respectively increase or decrease. In this manner, the actuator 1506 can achieve the adjustment A5.

FIG. 16 depicts a top plan view of an example wearable electronic device with another two-piece band system configured to retract toward the body of the wearable electronic device in response to an electrical signal from a tensioner. In many cases the tensioner can be coupled to one or more actuators that, in response to a signal from the tensioner, adjust the fit of the wearable electronic device.

The wearable electronic device 1600 can include a housing at that can be permanently or removably attached to a band that is illustrated as a two-part band system including a first band 1602 and a second band 1604. In the illustrated embodiment, a first actuator 1606 can be partially disposed within the first band 1602 and partially disposed within the housing of the wearable electronic device. Similarly, a second actuator 1608 can be partially disposed within a second band 1604 and partially within the housing of the wearable electronic device. Both the first actuator 1606 and the second actuator 1608 can be in electrical communication with a tensioner (not visible), which may be disposed within the housing of the wearable electronic device 1600.

In response to the increase or decrease in the size of the first actuator 1606 and the second actuator 1608, the band can experience an increase or decrease the tension with which the first band 1602 and the second band 1604 are coupled to the housing of the wearable electronic device 1600, which, in turn, can cause an increase or decrease the tightness of the fit of the band. In this manner, the first actuator 1606 and the second actuator 1608 can achieve the adjustment A4.

FIG. 17 depicts a top plan view of an example wearable electronic device with another two-piece band system configured to retract into the body of the wearable electronic device in response to an electrical signal from a tensioner. In many cases the tensioner can be coupled to one or more actuators that, in response to a signal from the tensioner, adjust the fit of the wearable electronic device.

The wearable electronic device 1700 can include a housing at that can be permanently or removably attached to a band that is illustrated as a two-part band system including a first band 1702 and a second band 1704. In the illustrated embodiment, an actuator 1706 can be formed as spring can be coupled between the first band 1702 and the second band 1704 through the housing of the wearable electronic device 1700. In some embodiments, the spring can be a passive spring. In other embodiments, the spring can be an active spring. For example, the spring can be made from a shape-memory material such as Nitinol. In such an embodiment, the tightness of a fit of the wearable electronic device 1700 can be maintained by the tensioner by applying an electrical current to the Nitinol.

In response to the increase or decrease in the tautness of the spring of the actuator 1706, can cause an increase or decrease the tightness of the fit of the band. In this manner, the actuator 1706 can achieve the adjustment A4.

Figure 18:
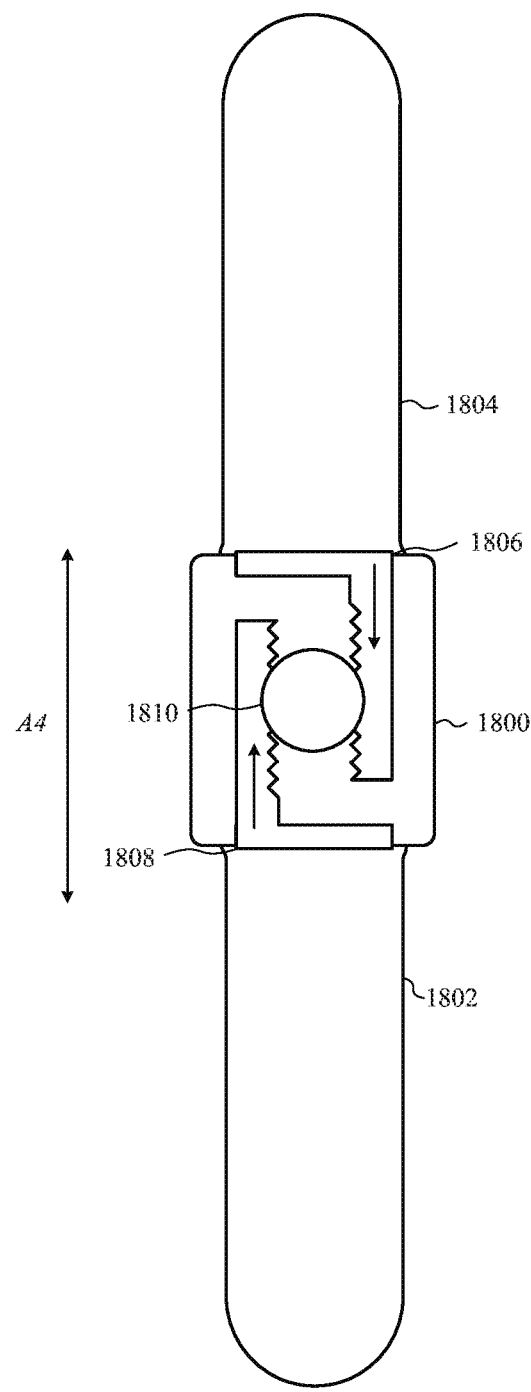
FIG. 18 depicts a top plan view of an example wearable electronic device with another two-piece band system configured to retract toward the body of the wearable electronic device in response to an electrical signal from a tensioner.

FIG. 18 depicts a top plan view of an example wearable electronic device with another two-piece band system configured to retract toward the body of the wearable electronic device in response to an electrical signal from a tensioner. In many cases the tensioner can be coupled to one or more actuators that, in response to a signal from the tensioner, adjust the fit of the wearable electronic device.

The wearable electronic device 1800 can include a housing at that can be permanently or removably attached to a band that is illustrated as a two-part band system including a first band 1802 and a second band 1804. In the illustrated embodiment, a first actuator 1806 can be partially disposed within the first band 1802 and partially disposed within the housing of the wearable electronic device. Similarly, a second actuator 1808 can be partially disposed within a second band 1804 and partially within the housing of the wearable electronic device. Both the first actuator 1806 and the second actuator 1808 can be in electrical communication with a tensioner (not visible), which may be disposed within the housing of the wearable electronic device 1800. In these examples, the first actuator 1806 and the second actuator 1808 can be worm gears (or other linear gears) that are in communication with a gear disposed within the housing of the wearable electronic device 1800.

In this manner, rotation of the gear can cause the first actuator 1806 and the second actuator 1808 to either extend or to retract into the housing. In many embodiments the gear can be coupled to electrical motor. In other examples, the gear can be coupled to a haptic feedback device disposed within the housing of the wearable electronic device 1800. As a result, the first band 1802 and the second band 1804 can extend or retract. In this manner, the first actuator 1806 and the second actuator 1808 can achieve the adjustment A4.

FIG. 19A depicts a top plan view of an example wearable electronic device with another two-piece band system configured to contract along its length in response to an electrical signal from a tensioner or in response to a user input. In many cases the tensioner can be coupled to one or more actuators that, in response to a signal from the tensioner, adjust the fit of the wearable electronic device.

The wearable electronic device 1900 can include a housing at that can be permanently or removably attached to a band that is illustrated as a two-part band system including a first band 1902 and a second band 1904. In the illustrated embodiment, a first actuator 1906 can be disposed within the first band. Similarly, a second actuator 1908 can be disposed within a second band 1904. The first actuator can be configured to be inserted into a buckle 1910, for example as shown in FIG. 19B.

Both the first actuator 1906 and the second actuator 1908 can be in electrical communication with a tensioner (not visible), which may be disposed within the housing of the wearable electronic device 1900.

In these examples, the first actuator 1906 and the second actuator 1908 can be worm gears (or other linear gears) that are in communication with a gear 1912 disposed within the buckle 1910. In this manner, rotation of the gear can cause the first actuator 1906 and the second actuator 1908 to either extend or to retract into the housing. In many embodiments the gear can be coupled to electrical motor. In other examples, the gear 1912 may be turned manually by a user. As a result, the first band 1902 and the second band 1904 can extend or retract. In this manner, the first actuator 1906 and the second actuator 1908 can achieve the adjustment A7.

Figure 20A:
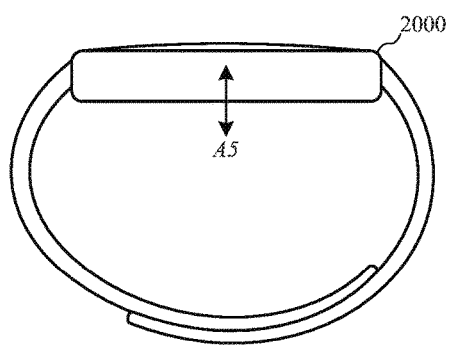
FIG. 20A depicts a side plan view of an example wearable electronic device with a movable housing configured to move toward or away from a user's skin in response to an electrical signal from a tensioner.
Figure 20B:
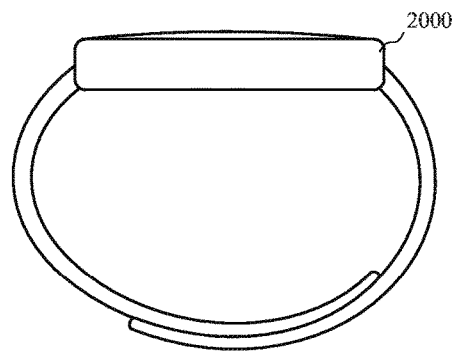
FIG. 20B depicts a side plan view of the example wearable electronic device of FIG. 20A, depicting the movable housing in an elevated position.

FIG. 20A depicts a side plan view of an example wearable electronic device with a movable housing configured to move toward or away from a user's skin in response to an electrical signal from a tensioner. The wearable electronic device 2000 can include a housing at that can be permanently or removably attached to a two-part band system. In the illustrated embodiment, the housing of the wearable electronic device 2000 can be configured to change the height of the housing of the wearable electronic device 2000 relative to a user's wrist and to the band, such as shown by the relative difference between FIG. 20A and FIG. 20B. In this manner, in response to the increase or decrease relative positioning of the band and the housing of the wearable electronic device 2000, the tightness of the fit of the wearable electronic device can respectively increase or decrease. In this manner, the wearable electronic device 2000 can achieve the adjustment A5.

Figure 21A:
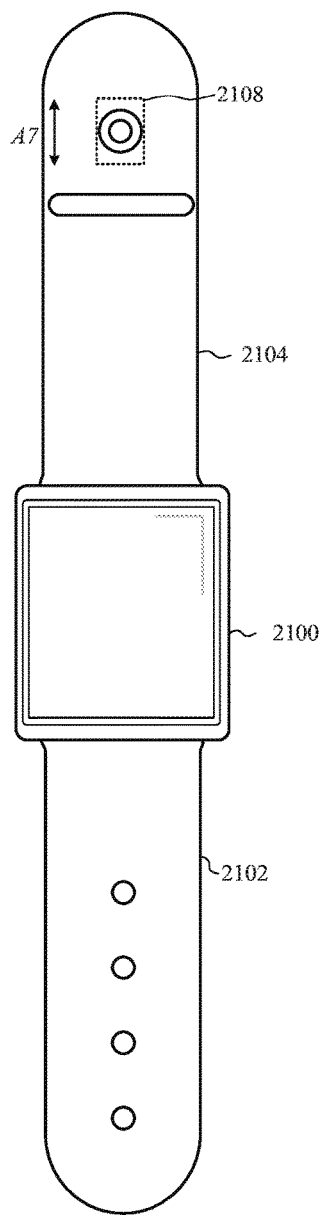
FIG. 21A depicts a top plan view of an example wearable electronic device with a pin and eyelet and interlacing band system configured such that the pin moves along the longitudinal axis of the band system in response to an electrical signal from a tensioner.
Figure 21B:
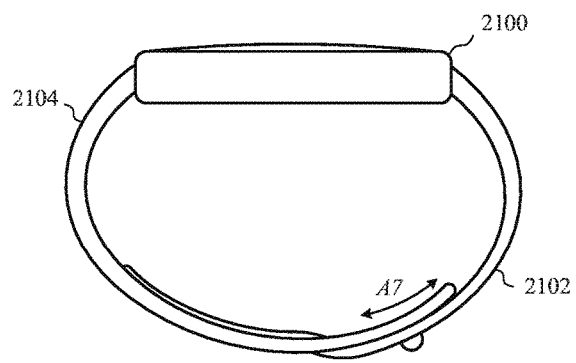
FIG. 21B depicts a side plan view of the example wearable electronic device of FIG. 21A.

FIG. 21A depicts a top plan view of an example wearable electronic device with a pin and eyelet and interlacing band system configured such that the pin moves along the longitudinal axis of the band system in response to an electrical signal from a tensioner. As illustrated, a first band 2102 and a second band 2104 can be overlapped in order to form a closed loop around a user's wrist. The first band 2102 can be coupled to the second band 2104 via a pin and eyelet attachment mechanism as substantially described herein. In this embodiment, an actuator 2108 can be coupled to the eyelet, which itself can be coupled to the tensioner. In response to an instruction to loosen or tighten the fit of the wearable electronic device 2100, the tensioner can cause the actuator 2108 to move the eyelet along the longitudinal axis of the second band 2104. In this manner, the actuator 2108 to can achieve the adjustment A7, as shown for example in FIG. 21B.

Figure 22:
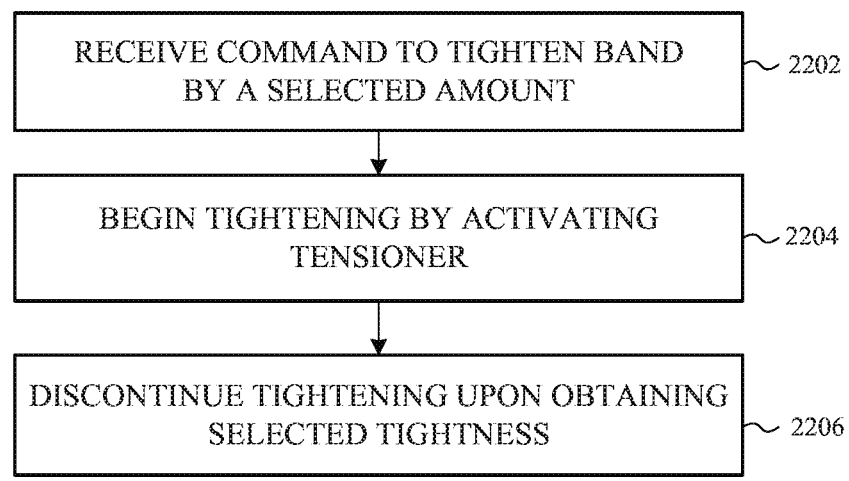
FIG. 22 is a flow chart that depicts example operations of a method of tightening the fit of a wearable electronic device.

FIG. 22 is a flow chart that depicts example operations of a method of tightening the fit of a wearable electronic device. The method can begin at operation 2202 in which a command is received to tighten a band of a wearable electronic device by a selected amount. In some examples, the selected amount can be a value or pointer corresponding to an amount or magnitude of tightness change, either relative or absolute. For example, the value or pointer can indicate that the fit should be tightened by 5%.

In another example, the value or pointer can indicate that the fit should be tightened by shortening a band by 1 mm. In another example, the value or pointer can indicate that the fit should be tightened by applying a force of 0.1 Newtons to the band. In other embodiments, other values and/or pointers may be used.

The method can continue to operation 2204 in which a tensioner is activated to begin tightening the band. Next, at operation 2206, tightening can be discontinued after the selected amount of tightness increase is obtained. In other embodiments, the method depicted in FIG. 22 can be implemented by first received a command to loosen the band by a particular amount.

Figure 23:
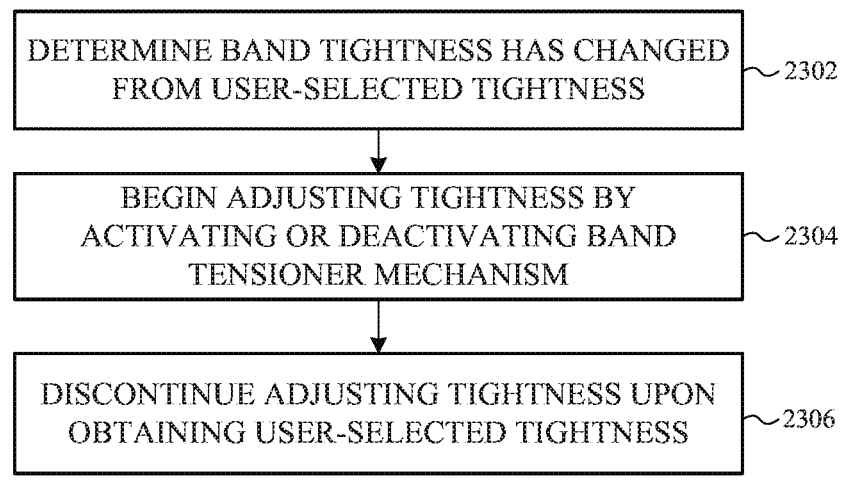
FIG. 23 is a flow chart that depicts example operations of a method of dynamically adjusting the fit of a wearable electronic device.

FIG. 23 is a flow chart that depicts example operations of a method of dynamically adjusting the fit of a wearable electronic device. The method can begin at operation 2302 during which a signal can be received that indicates the band tightness has changed from a previously obtained or determined user-selected tightness. For example, in some embodiments, a sensor coupled to a band of the wearable electronic device can periodically, continuously, or on request measure the strain within the band. Thereafter, the strain measurement can be correlated to (via a formula, algorithm output, or look-up table) what degree of tightness the measured strain corresponds to. In some examples strain can be measured with a piezoresistive strain sensor. Upon determining that the current tightness of the band does not match (or has been measured to be outside a threshold range of tightnesses), the method can continue to operation 2304 in which the tightness of the band can be adjusted by either activating or deactivating a tensioner mechanism such as an actuator that is mechanically coupled to the band itself. Thereafter, tightening or loosening can be terminated at operation 2306, once the necessary tightness is obtained.

In many cases the threshold, threshold range, and/or other user-selected setting for tightness of the band can be obtained from a memory associated with the wearable electronic device. In other examples, the user setting can be obtained from a third-party device, or a separate electronic device in communication with the wearable electronic device.

Figure 24:
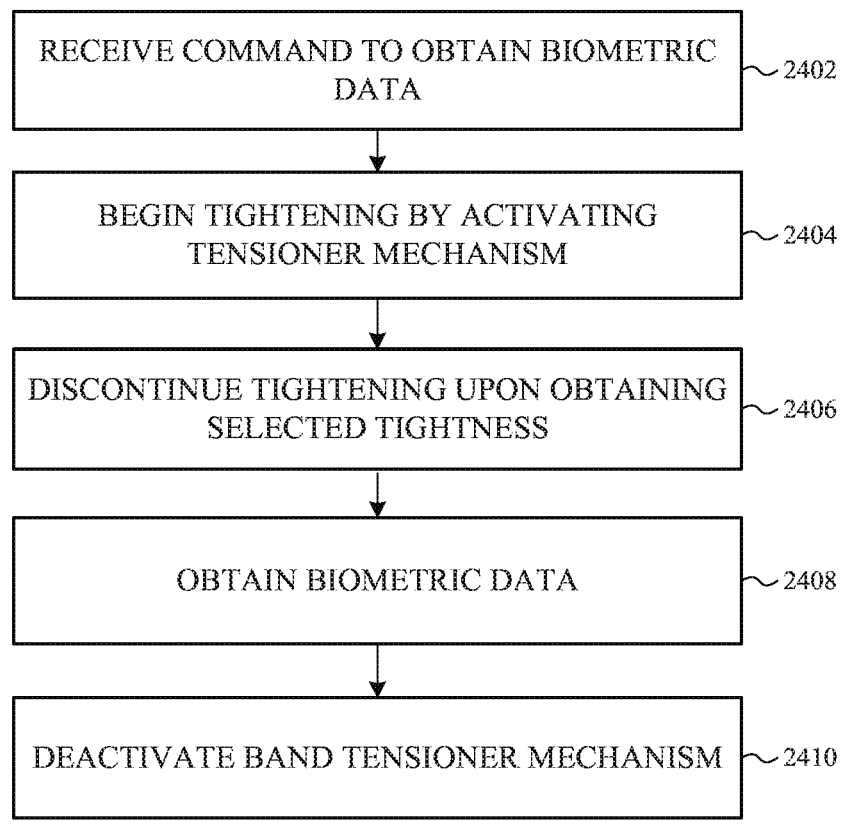
FIG. 24 is a flow chart that depicts example operations of a method of dynamically adjusting the fit of a wearable electronic device prior to obtaining biometric data with a biometric sensor.

FIG. 24 is a flow chart that depicts example operations of a method of dynamically adjusting the fit of a wearable electronic device prior to obtaining biometric data with a biometric sensor. The method can begin at operation 2402 in which a command is received to obtain biometric data, such as a user's pulse. Next, at operation 2404, a tightening mechanism associated with the wearable electronic device can be activated in order to increase the tightness of the wearable electronic device against the measurement site for obtaining a biometric data measurement. Next, at operation 2406, tightening can be discontinued once it is determined that a tightness sufficient for obtaining biometric data is obtained. Next, at operation 2408, biometric data can be obtained. Finally, at operation 2410, the previously-applied tension can be released, and the band can be restored to its original tightness.

Figure 25:
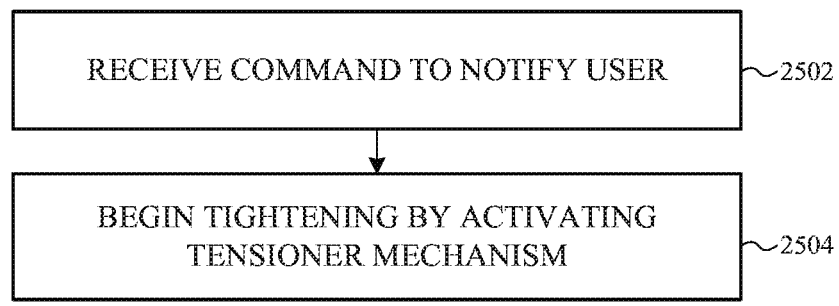
FIG. 25 is a flow chart that depicts example operations of a method of dynamically adjusting the fit of a wearable electronic device as a means of soliciting a user's attention.

FIG. 25 is a flow chart that depicts example operations of a method of dynamically adjusting the fit of a wearable electronic device as a means of soliciting a user's attention. The method can begin at operation 2502 by receiving a command to notify a wearer of the wearable electronic device. Next, at operation 2504, the wearable electronic device can be tightened.

Figure 26:
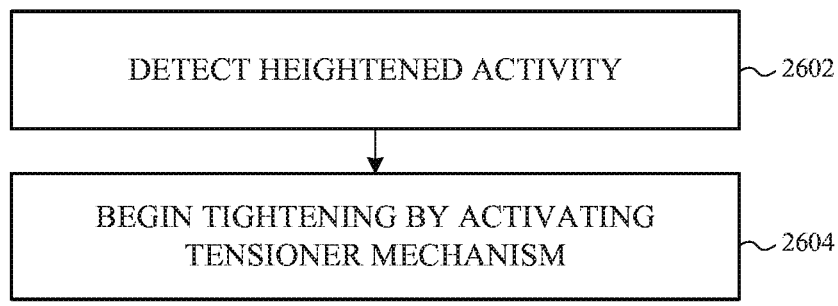
FIG. 26 is a flow chart that depicts example operations of a method of dynamically adjusting the fit of a wearable electronic device in response to heightened user activity.

FIG. 26 is a flow chart that depicts example operations of a method of dynamically adjusting the fit of a wearable electronic device in response to heightened user activity. The method can begin at operation 2602 by receiving an indication that the user is engaged in heighted activity. For example, in some embodiments, heighted user activity can be detected by monitoring the output from one or more accelerometers, gyroscopes, inertial measurement units, global positioning sensors, proximity sensors, and the link. Next, at operation 2604, the wearable electronic device can be tightened to prevent sliding during the heightened activity.

Many embodiments of the foregoing disclosure may include or may be described in relation to various methods of operation, use, manufacture, and so on. Notably, the operations of methods presented herein are meant only to be exemplary and, accordingly, are not necessarily exhaustive. For example an alternate operation order, or fewer or additional steps may be required or desired for particular embodiments.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not meant to be exhaustive or to limit the embodiments to the precise forms disclosed. It will be apparent to one of ordinary skill in the art that many modifications and variations are possible in view of the above teachings. In particular, any features described with respect to one embodiment may also be used in other embodiments, where compatible. Likewise, the features of the different embodiments may be exchanged, substituted, or omitted where compatible and appropriate.

We claim:

1. A watch comprising:
a housing containing a processor;
a first band portion extending from the housing;
a second band portion extending from the housing; and
a coupling for connecting the first band portion to the second band portion to form a loop for holding the housing against a wrist of a user, wherein the coupling is configured to, in response to a signal from the processor, adjust an amount of overlap between the first band portion and the second band portion.

2. The watch of claim 1, wherein:
the first band portion comprises a first actuator; and
the second band portion comprises multiple second actuators, wherein the first actuator and one of the second actuators form the coupling.

3. The watch of claim 1, wherein:
the first band portion comprises a permanent magnet; and
the second band portion comprises multiple electromagnetic coils, wherein the permanent magnet and one of the electromagnetic coils form the coupling.

4. The watch of claim 1, wherein:
the first band portion comprises an actuator, wherein the actuator is moveable along a longitudinal length of the first band portion; and
the second band portion comprises multiple attachment mechanisms, wherein the actuator and one of the attachment mechanisms form the coupling.

5. The watch of claim 1, wherein the coupling comprises a gear that engages the first band portion and the second band portion, wherein rotation of the gear adjusts the amount of overlap between the first band portion and the second band portion.

6. A watch comprising:
a housing containing a processor;
a band positioned partially within the housing and extending away from the housing; and
an actuator configured to, in response to a signal from the processor, adjust an amount of the band that is within the housing.

7. The watch of claim 6, wherein the band is connected to the housing via the actuator.

8. The watch of claim 6, wherein the actuator is formed in a serpentine pattern and is configured to contract in response to the signal from the processor.

9. The watch of claim 6, wherein the housing forms a channel receiving the amount of the band.

10. The watch of claim 6, wherein the actuator is of a shape memory wire.

11. The watch of claim 6, wherein the band comprises a first band portion and a second band portion configured to be coupled together to form a loop.

12. The watch of claim 11, wherein:
the actuator is a first actuator between the first band portion and the housing; and
the band comprises a second actuator between the first band portion and the housing and configured to, in response to the signal from the processor, adjust an amount of the second band portion that is within the housing.

13. The watch of claim 11, wherein the housing comprises:
a first channel receiving the amount of the first band portion; and
a second channel receiving the amount of the second band portion.

14. A watch comprising:
a housing containing a processor;
a band extending from opposing sides of the housing to form a loop for extending about a wrist of a user; and
an actuator configured to, in response to a signal from the processor, adjust a length of the band such that a tightness of the loop about the wrist is adjusted, wherein the actuator is formed in a serpentine pattern and is configured to contract in response to the signal from the processor.

15. The watch of claim 14, wherein the band forming the loop comprises a first band portion and a second band portion.

16. The watch of claim 15, wherein the actuator is a first actuator within the first band portion and the band comprises a second actuator within the second band portion.

17. The watch of claim 14, wherein the actuator is disposed around a perimeter of the band.

18. The watch of claim 14, wherein the actuator is of a shape memory wire.

19. The watch of claim 14, further comprising a biometric sensor operably coupled to the processor, wherein the processor is configured, in response to receiving an instruction to obtain biometric data, to send the signal to the actuator to adjust the length of the band prior to obtaining the biometric data from the biometric sensor.

* * * * *